US011383038B2

(12) United States Patent
Nazzaro et al.

(10) Patent No.: US 11,383,038 B2
(45) Date of Patent: Jul. 12, 2022

(54) PRE-FILLED CARTRIDGE-BASED DRUG DELIVERY DEVICE

(71) Applicant: Insulet Corporation, Acton, MA (US)

(72) Inventors: David Nazzaro, Groveland, MA (US); Ian McLaughlin, Boxboro, MA (US); Maureen McCaffrey, Boston, MA (US); Simon Kozin, Lexington, MA (US); Jackie Mac, Malden, MA (US)

(73) Assignee: INSULET CORPORATION, Acton, MA (US)

( * ) Notice: Subject to any disclaimer, the term of this patent is extended or adjusted under 35 U.S.C. 154(b) by 849 days.

(21) Appl. No.: 16/140,186

(22) Filed: Sep. 24, 2018

(65) Prior Publication Data

US 2019/0091404 A1 Mar. 28, 2019

Related U.S. Application Data

(60) Provisional application No. 62/562,807, filed on Sep. 25, 2017.

(51) Int. Cl.
*A61M 5/20* (2006.01)
*A61M 5/315* (2006.01)
(Continued)

(52) U.S. Cl.
CPC ...... *A61M 5/2033* (2013.01); *A61M 5/14244* (2013.01); *A61M 5/14248* (2013.01);
(Continued)

(58) Field of Classification Search
CPC .............. A61M 5/2033; A61M 5/3157; A61M 2005/2006; A61M 2205/581;
(Continued)

(56) References Cited

U.S. PATENT DOCUMENTS 2,833,007 A 5/1958 Messer
4,307,713 A 12/1981 Galkin et al.
(Continued)

FOREIGN PATENT DOCUMENTS

CN 1898131 A 1/2007
EP 2099384 A1 * 9/2009 ......... A61B 5/14503
(Continued)

OTHER PUBLICATIONS

International Search Report and Written Opinion for PCT/US17/061095, dated Feb. 20, 2018, 8 pages.
(Continued)

*Primary Examiner* — Bhisma Mehta
*Assistant Examiner* — Neeraja Gollamudi
(74) *Attorney, Agent, or Firm* — Goodwin Procter LLP

(57) ABSTRACT

A wearable drug delivery device that can deliver a liquid drug stored in a container to a patient is provided. The container can be a prefilled cartridge that can be loaded into the drug delivery device by the patient or that can be preloaded within the drug delivery device when provided to the patient. A sealed end of the container is pierced to couple the stored liquid drug to a needle conduit that is coupled to a needle insertion component that provides access to the patient. A drive system of the drug delivery device can expel the liquid drug from the cartridge to the patient through the needle conduit. The drive system can be controlled to provide the liquid drug to the patient in a single dose or over multiple doses.

20 Claims, 25 Drawing Sheets

(51) Int. Cl.
*A61M 5/158* (2006.01)
*A61M 5/145* (2006.01)
*A61M 5/142* (2006.01)
A61M 5/00 (2006.01)
A61M 5/28 (2006.01)
A61M 5/24 (2006.01)

(52) U.S. Cl.
CPC .......... *A61M 5/3157* (2013.01); *A61M 5/001* (2013.01); *A61M 5/1454* (2013.01); *A61M 5/288* (2013.01); *A61M 2005/14256* (2013.01); *A61M 2005/1581* (2013.01); *A61M 2005/2006* (2013.01); *A61M 2005/2073* (2013.01); *A61M 2005/2474* (2013.01); *A61M 2005/31518* (2013.01); *A61M 2205/581* (2013.01); *A61M 2205/582* (2013.01)

(58) Field of Classification Search
CPC .. A61M 2205/582; A61M 5/14; A61M 5/158; A61M 5/142; A61M 5/14244; A61M 5/145; A61M 5/1452; A61M 5/1454; A61M 2005/1585; A61M 2005/206; A61M 2005/2073
See application file for complete search history.

(56) References Cited

U.S. PATENT DOCUMENTS

| | | | |
|---|---|---|---|
| 4,416,663 | A | 11/1983 | Hall |
| 4,801,957 | A | 1/1989 | Vandemoere |
| 4,850,954 | A | 7/1989 | Charvin |
| 4,882,600 | A | 11/1989 | Van de Moere |
| 4,973,998 | A | 11/1990 | Gates |
| 5,045,871 | A | 9/1991 | Reinholdson |
| 5,239,326 | A | 8/1993 | Takai |
| 5,452,033 | A | 9/1995 | Balling et al. |
| 5,576,781 | A | 11/1996 | Deleeuw |
| 5,899,882 | A | 5/1999 | Waksman et al. |
| 6,164,044 | A | 12/2000 | Porfano et al. |
| 6,685,452 | B2 | 2/2004 | Christiansen et al. |
| 6,767,319 | B2 | 7/2004 | Reilly et al. |
| 7,182,726 | B2 | 2/2007 | Williams et al. |
| 7,303,073 | B2 | 12/2007 | Raynal-Olive et al. |
| 8,056,719 | B2 | 11/2011 | Porret et al. |
| 8,105,282 | B2 | 1/2012 | Susi et al. |
| 8,461,561 | B2 | 6/2013 | Freeman et al. |
| 8,727,117 | B2 | 5/2014 | Maasarani |
| 9,005,166 | B2 | 4/2015 | Uber, III et al. |
| 9,248,229 | B2 | 2/2016 | Devouassoux et al. |
| 9,427,710 | B2 | 8/2016 | Jansen |
| 9,555,911 | B2 | 1/2017 | Pawlowski et al. |
| 9,598,195 | B2 | 3/2017 | Deutchle et al. |
| 9,862,519 | B2 | 1/2018 | Deutchle et al. |
| 10,086,131 | B2 | 10/2018 | Okihara |
| 10,342,926 | B2 | 7/2019 | Nazzaro et al. |
| 2004/0139698 | A1 | 7/2004 | Grifols |
| 2005/0222539 | A1* | 10/2005 | Gonzales ............ A61M 5/3157 604/207 |
| 2006/0086909 | A1 | 4/2006 | Schaber |
| 2009/0254041 | A1 | 10/2009 | Krag et al. |
| 2014/0163664 | A1 | 6/2014 | Goldsmith |
| 2015/0057613 | A1 | 2/2015 | Clemente et al. |
| 2015/0078961 | A1 | 3/2015 | Opie |
| 2015/0196720 | A1 | 7/2015 | Okihara et al. |
| 2016/0262984 | A1 | 9/2016 | Arnott et al. |
| 2017/0197028 | A1 | 7/2017 | Goldsmith |

FOREIGN PATENT DOCUMENTS

| | | |
|---|---|---|
| EP | 2099384 A1 | 9/2009 |
| ES | 2559866 T3 | 2/2016 |
| GB | 2461086 A | 12/2009 |
| JP | H09010282 A | 1/1997 |
| JP | 2002126039 A | 5/2002 |
| JP | 2007516775 A | 6/2007 |
| WO | 2007039930 A1 | 4/2007 |
| WO | 2017089289 A1 | 6/2017 |
| WO | 2017205816 A1 | 11/2017 |
| WO | 2018075851 A2 | 4/2018 |

OTHER PUBLICATIONS

International Search Report and Written Opinion for PCT/US18/52468, dated Feb. 26, 2019, 16 pages.
International Preliminary Report on Patentability for the International Patent Application No. PCT/US2017/061095, dated May 23, 2019, 7 pages.

* cited by examiner

PRE-FILLED CARTRIDGE-BASED DRUG DELIVERY DEVICE

PRIORITY

This application claims the benefit of priority under 35 USC § 119 to U.S. Provisional Patent Application Ser. No. 62/562,807, filed Sep. 25, 2017, which is incorporated by reference herein in its entirety and for all purposes.

TECHNICAL FIELD

Embodiments generally relate to medication delivery. More particularly, embodiments relate to wearable drug delivery devices.

BACKGROUND

Many conventional drug delivery systems, such as handheld auto-injectors, are designed to rapidly delivery a drug to a patient. These conventional drug delivery systems are generally not suitable for delivering a drug to a user over relatively longer periods of time as may be required for many drugs.

As an alternative to conventional auto-injectors, many conventional drug delivery systems are designed to be wearable and to deliver a drug more slowly to the patient. However, these conventional wearable drug delivery systems often require a patient to transfer a drug or other medicine from a vial to a container within the drug delivery system. Transferring the drug can be a challenging task for many patients as it may require precise handling of the drug, a transfer mechanism (e.g., a syringe), and the drug delivery system. Some conventional wearable drug delivery systems use prefilled cartridges that contain the drug intended for the patient, obviating the need for such drug transfers. However, these conventional cartridge-based drug delivery systems are often bulky and cumbersome due to the included cartridge and can be uncomfortable when worn by the patient.

A need therefore exists for a more convenient and user-friendly wearable drug delivery device for providing a drug to a user.

SUMMARY

In one aspect of the present invention, a drive spring release mechanism for use with a drug delivery device may have a drug container for storing a liquid drug. A first end of the drug container may be sealed by a plunger. A needle conduit may be coupled to the drug container. A needle insertion component may be coupled to the needle conduit. A drive mechanism may be coupled to the plunger. The drive mechanism may include a drive spring and at least one force transfer element. The spring retention mechanism may include a drive mechanism lock. The spring retention mechanism may include a spring retainer. The spring retention mechanism may include a drive mechanism release. The spring retainer may have first and second longitudinally extending spring arms that may extend to engage a cam surface of the drive mechanism release. When the drive spring release mechanism is in a locked state, the cam surface may force distal ends of the spring arms outward so that portions of the distal ends may engage associated stop surfaces of the drive mechanism lock, thereby capturing the drive spring therebetween to maintain the drive spring in a compressed state. When the drive spring release mechanism is in an unlocked state, the drive spring release mechanism may be rotated from its position in the locked state, so that the cam surface may release the distal ends of the spring arms such that they may flex inward toward each other such that the distal ends of the spring arms may clear the stop surfaces of the drive mechanism lock, thereby releasing the drive spring so that it may expand. Releasing the drive spring so that it may expand allows the drive spring to push the spring retainer, which may push the force transmitting elements into the liquid drug container to dispense the liquid drug contained in the liquid drug container. A cam extension may extend longitudinally from the drive mechanism release. The cam extension may have a width less than a distance between the arms in the unlocked state. The portions of the distal ends of each spring arm may be a jog from a substantially longitudinal direction, to a substantially radial direction, to a substantially longitudinal direction. A portion of the jog in the substantially radial direction may engage the stop surface of the drive mechanism lock in the locked state. An arm extension may extend radially from an end of the drive mechanism lock that may be configured for radial translation.

In another aspect, a drug delivery device may include a drug container for storing a liquid drug. A first end of the drug container may be sealed by a plunger. A needle conduit may be coupled to the drug container. A needle insertion component may be coupled to the needle conduit. A drive mechanism may be coupled to the plunger. The drive mechanism may include a drive spring and may include a plurality of cylindrical force transfer elements. The drive mechanism may include a track for guiding the plurality of cylindrical force transfer elements. Each of the plurality of cylindrical force transfer elements may include a cylindrical portion having a groove. The track may have at least one guide rail disposed on the track. The guide rail may be receivable within the grooves of the plurality of cylindrical force transfer elements. A torsion spring may engage the needle insertion component. A trigger lock may engage the needle insertion component and may resist the torsion spring. The track may have a straight portion and the track may have a curved portion. The at least one guide rail may be a first guide rail and a second guide rail disposed on opposing sides of the track on the straight portion. The curved portion may not include the first and second guide rails.

In another aspect, an activation element for a drug delivery device may include a user activation element coupled to a top portion of a drug delivery device. The user activation feature may include a protrusion disposed on an interior-facing portion of the user activation element. The protrusion may include an expanded diameter portion for interacting with a recess associated with a button lock structure within the drug delivery device so that when the user activation element is depressed, the recess captures the expanded diameter portion so that the user activation element remains depressed. The user activation element may include an elastomeric button.

In another aspect, a carrier for engaging a liquid drug container and a needle conduit that is coupled to the liquid drug container may include a first portion that may be for engaging a cylindrical body portion of the liquid drug container. A second portion may be for engaging a neck of the liquid drug container. A third portion may be for engaging the needle conduit at a plurality of locations along a length of the needle conduit. A plurality of features may be for maintaining the liquid drug container and the needle conduit in a desired position during a sterilization operation. A fourth portion for engaging a sterile barrier may be coupled to the needle conduit. The fourth portion may include first and second halves that encapsulate the sterile barrier during the sterilization operation. A weighing feature may extend from an end of the carrier opposing an open end of a liquid drug container. The weighing feature may be configured to support the carrier in an upright configuration such that the weighing feature is an only point of contact with another surface. The weighing feature may be located at a radial center of gravity of the carrier when the carrier is in the upright configuration. The plurality of features for maintaining the liquid drug container and the needle conduit in a desired position may include a plurality of recesses that may have an inner width smaller than a diameter of the needle conduit.

In another aspect, a method of operating a drug delivery device may include an on-body interlock device of the drug delivery device that may be engaged by pressing and/or adhering the drug delivery device to a patient. A user engagement feature of the drug delivery device may be pressed by the user. A needle insertion mechanism of the drug delivery device may be activated to advance the needle and a soft cannula. A needle retraction mechanism of the drug delivery device may retract the needle, leaving the soft cannula in place. A septum piercing mechanism of the drug delivery device may move the needle conduit to pierce a septum of the liquid drug container, that may expose liquid drug within the liquid drug container to the needle conduit. A drive spring release mechanism of the drug delivery device may be activated to release a drive spring of the drug delivery device. A plurality of force transmitting elements may be coupled to the drive spring. The plunger may press the plunger into the liquid drug container to expel the liquid drug out through the needle conduit. When liquid drug may be expelled from the liquid drug container, a tactile feedback may be provided to the user.

DETAILED DESCRIPTION

This disclosure presents various systems, components, and methods for delivering a liquid drug or medicine to a patient or user. Each of the systems, components, and methods disclosed herein provides one or more advantages over conventional systems, components, and methods.

Various embodiments include a wearable drug delivery device that can deliver a liquid drug stored in a container to a patient or user. The container can be a prefilled cartridge that can be loaded into the drug delivery device by the patient or that can be preloaded within the drug delivery device when provided to the patient. A sealed end of the container can be pierced to couple the stored liquid drug to a needle conduit. The needle conduit can be coupled to a needle insertion component that provides access to the patient. A drive system of the drug delivery device can expel the liquid drug from the container to the patient through the needle conduit. The drive system can be controlled to provide the liquid drug to the patient in a single dose or over multiple doses. The drive system can include an energy storage component and an energy transfer component to enable the drug delivery device to maintain a small form factor. As a result, the patient's comfort when using the drug delivery device is improved. Other embodiments are disclosed and described.

Figure 1:
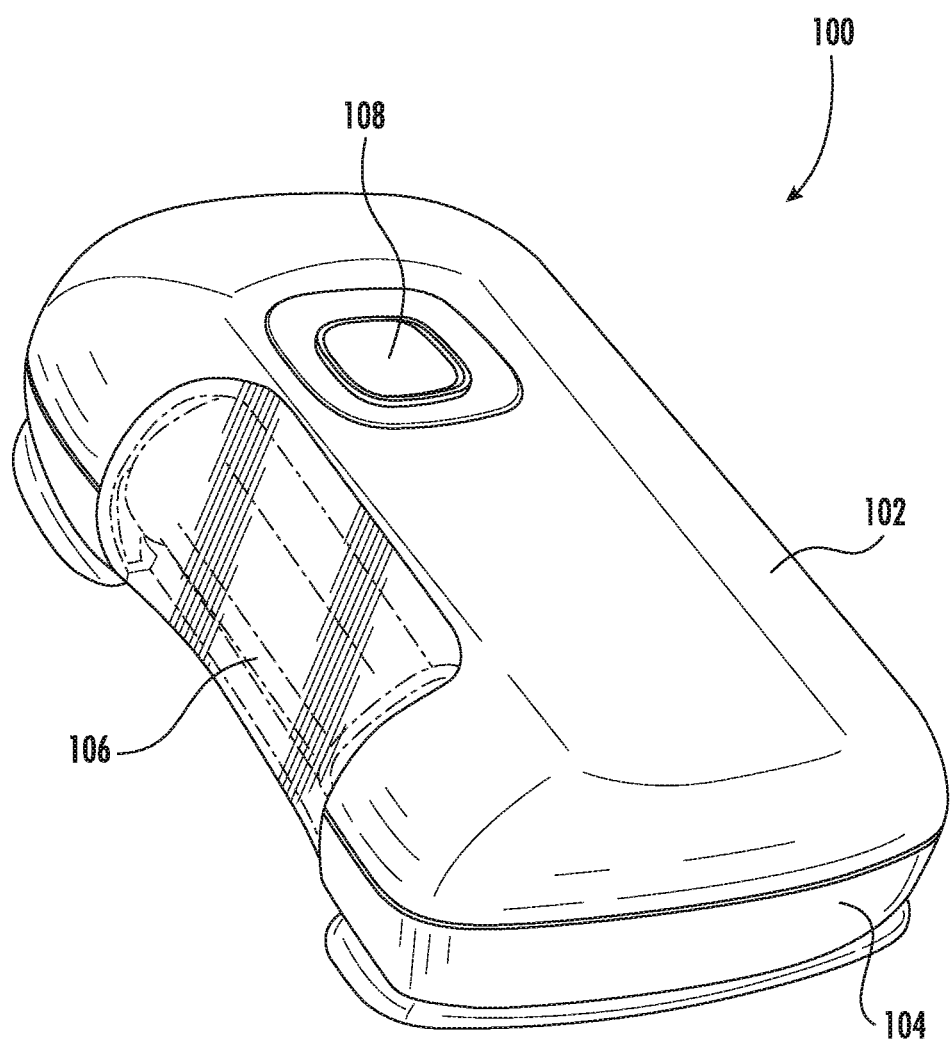
FIG. 1 illustrates an isometric view of a first exemplary embodiment of a drug delivery device, in accordance with an embodiment of the present disclosure.
Figure 2:
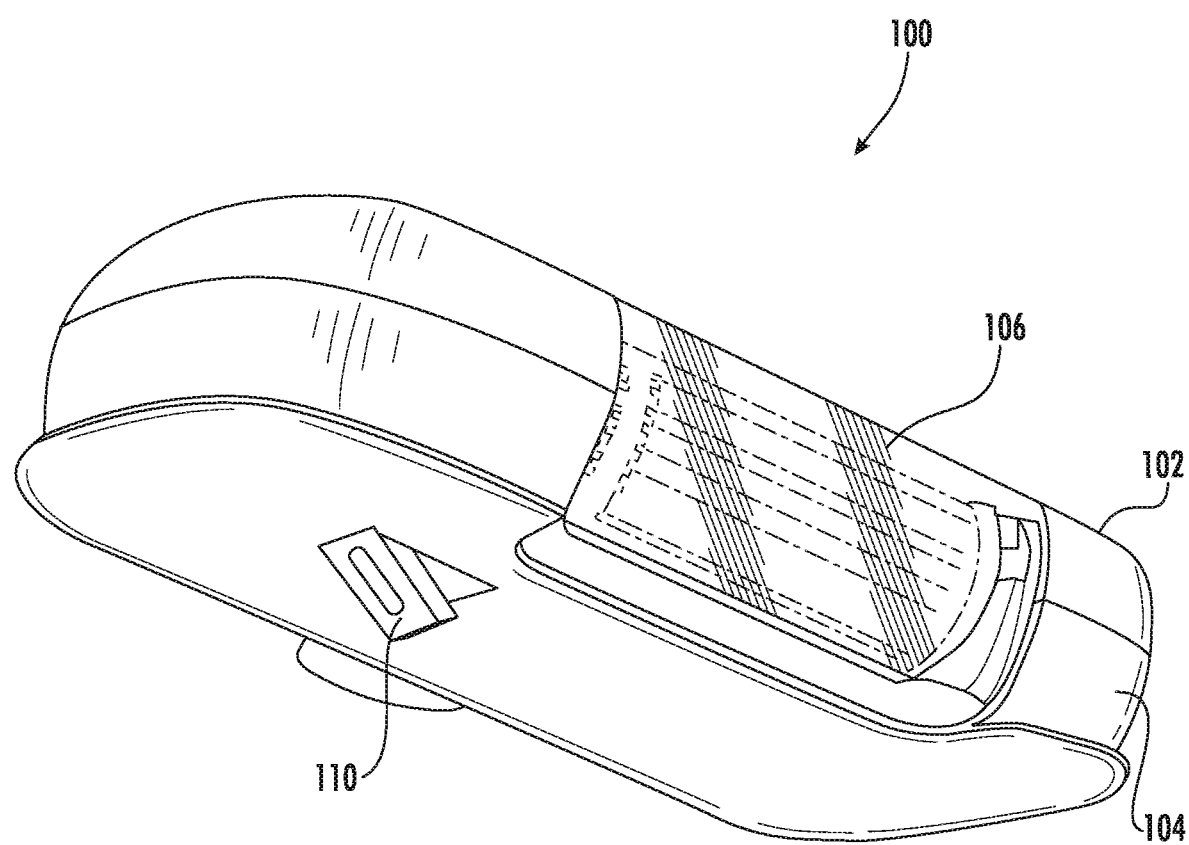
FIG. 2 illustrates a second isometric view of the drug delivery device of FIG. 1.

FIGS. 1 and 2 illustrate an embodiment of a drug delivery device 100. The drug delivery device 100 can include a top or upper portion 102 and a lower portion or base 104. The top portion 102 and the lower portion 104 can together form a housing of the drug delivery device 100. The top portion 102 and the lower portion 104 can be coupled together to form an outside of the drug delivery device 100. The drug delivery device 100 can represent another design or form factor of the drug delivery device 100.

The drug delivery device 100 can include an opening 106 that can expose a portion of a drug container (e.g., a cartridge) positioned within the drug delivery device 100. The opening 106 can allow visual inspection and monitoring of the drug container. For example, a patient of the drug delivery device 100 can monitor an amount of liquid drug remaining in the drug container. In this way, a patient can monitor dosing status. The opening 106 can also enable a patient to inspect the liquid drug for particles or discoloration. The opening 106 can be covered with a clear material such as plastic to allow a viewing of the drug container. The opening 106 can be of any size or shape and can be positioned along any portion of the drug delivery device 100. Further details relating to the opening 106 and exemplary coverings therefore will be described below in relation to FIG. 15.

The top portion 102 of the drug delivery device 100 can include a patient interaction element or component 108. In various embodiments, the patient interaction element 108 can be a push button. In various embodiments, the patient interaction element 108 can correspond to the patient interaction element 108. The patient interaction element 108 can be used to activate the drug delivery device 100. For example, when a patient presses on the patient interaction element 108, the drug delivery device 100 can begin delivering the stored liquid drug to the patient. In various embodiments, the patient interaction element 108 can be used to start and stop delivery of the liquid drug to the patient to enable a patient to dispense multiple doses of the liquid drug.

In various embodiments, the drug delivery device 100 can include two or more patient interaction elements. In various embodiments, the drug delivery device 100 can also include an on-body interlock device 110. The opening 106 can be positioned on a side of the upper portion 102 and lower portion 104 of the drug delivery device.

The drug delivery device 100 can include an on-body interlock 110. The on-body interlock 110 can also extend from the bottom portion 104 along any portion of the bottom portion 104. The on-body interlock 110 can be a button or switch that can retract into the drug delivery device 100 when the lower portion 104 is coupled to the patient.

The on-body interlock device 110 can be required to be depressed (e.g., passively) before the drug delivery device 100 can be activated. For example, when the drug delivery device 100 is coupled to a patient, the on-body interlock device 110 can be passively depressed. Once depressed, the patient interaction element 108 can subsequently be used to activate the drug delivery device 100. Prior to the on-body interlock 110 being depressed, the patient interaction element 108 can be disengaged such that manipulation of the patient interaction element 108 does not activate the drug delivery device 100.

The on-body interlock 110 can also stop operation of the drug delivery device 100. For example, when the drug delivery device 100 is removed from a patient, the on-body interlock 110 can be biased to extend from the lower portion 104. When so extended, the on-body interlock 110 can place the drug delivery device 110 into a stopped or idle state of operation that prevents or stops delivery of the liquid drug to the patient.

The on-body interlock 110 can be any component that can be biased to extend from the drug delivery device 100 and that can be retracted inside of the drug delivery device 100 when a force is applied. The on-body interlock 110 can be implemented as a pivoting component, biased to remain outside of the drug delivery device 100 and to pivot into the drug delivery device 100 when passively depressed. In various other embodiments, the on-body interlock 110 can be implemented as a push rod.

Figure 3:
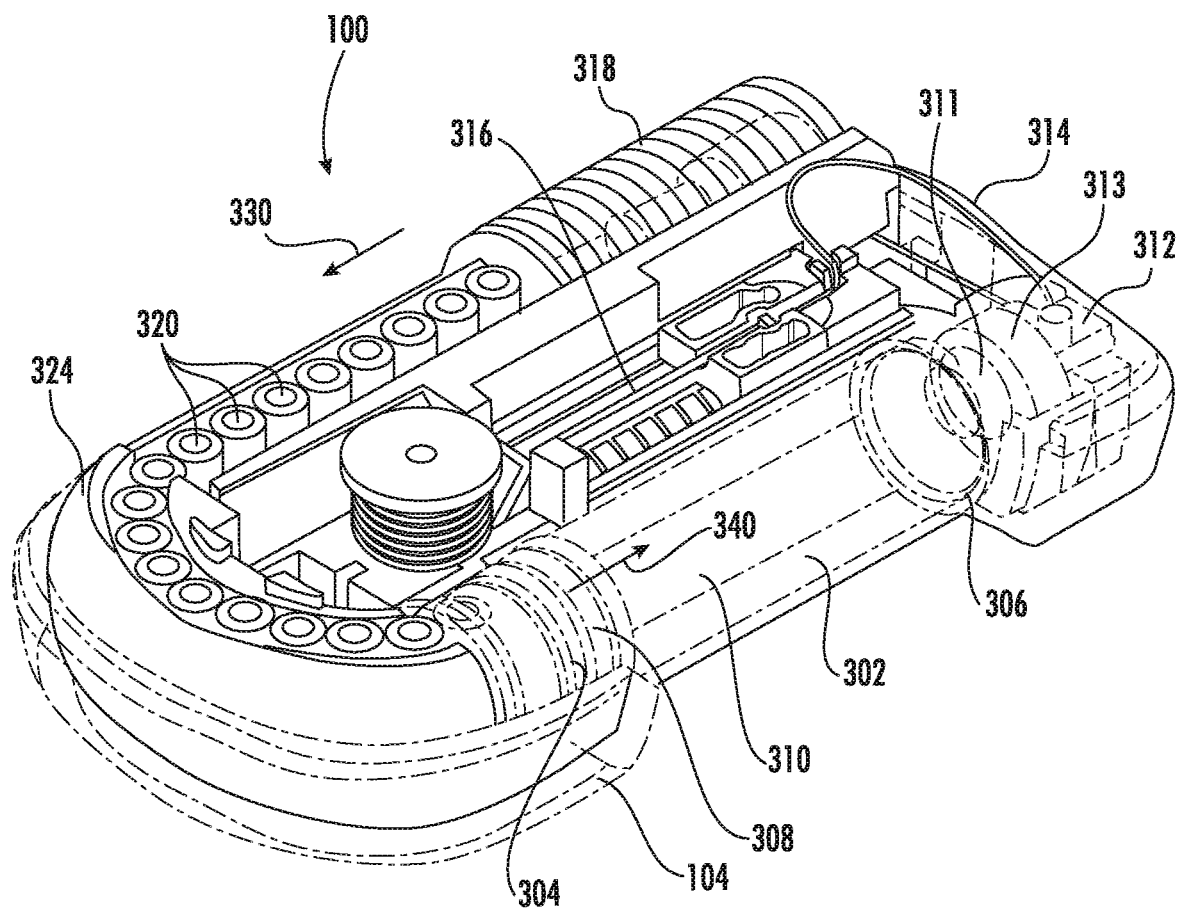
FIGS. 3 and 4 illustrate isometric views of the drug delivery device of FIG. 1 with a cover portion removed.
Figure 4:
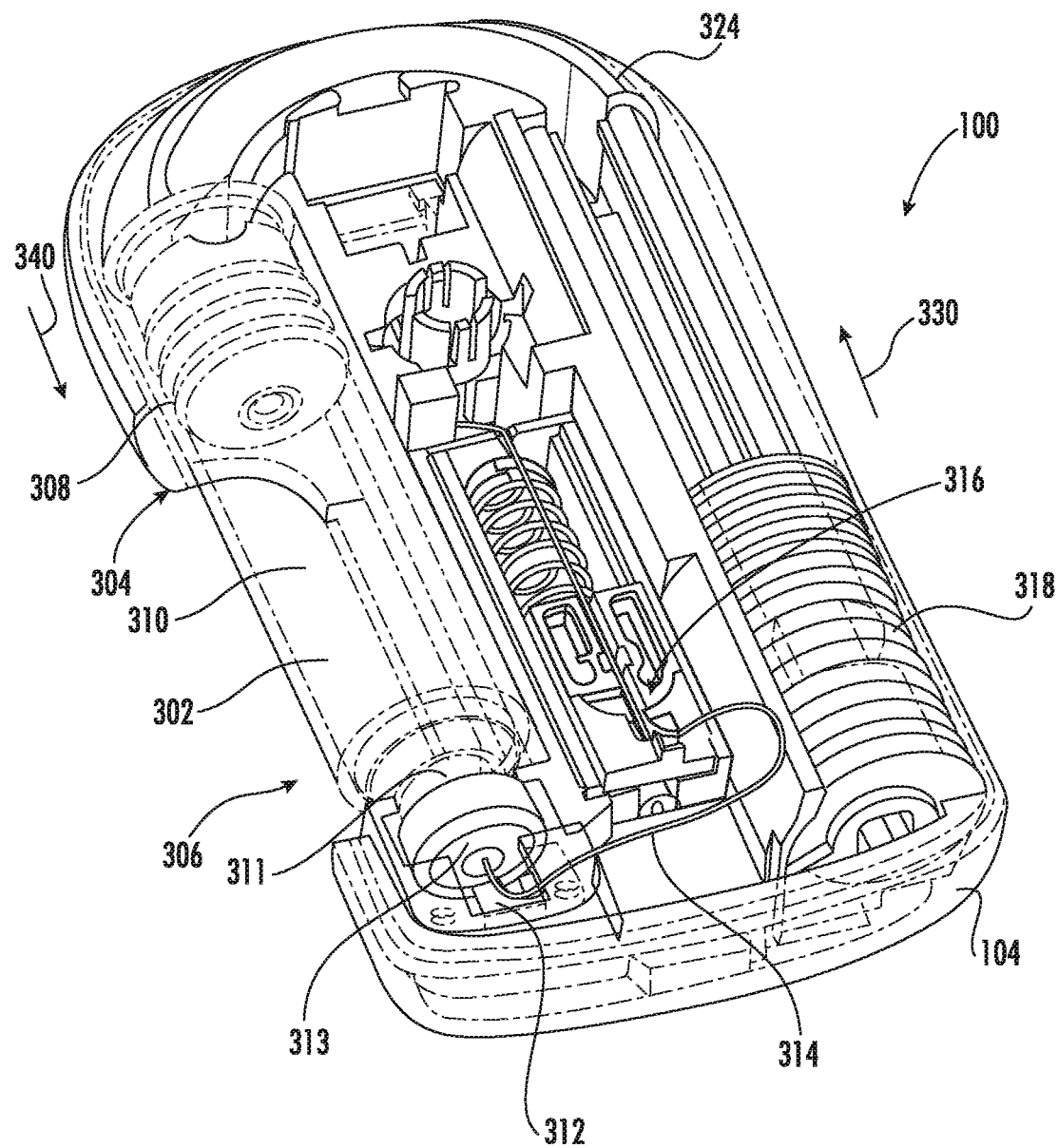

FIGS. 3 and 4 illustrate a first exemplary arrangement of internal components of the drug delivery device 100. The drug delivery device 100 can include a drug container 302. The drug container 302 can include a first end 304 and a second end 306. The drug container 302 can be sealed at or near the first end 304 and the second end 306. The drug container 302 can be formed from glass and/or plastic. The first end 304 can include a plunger 308. The second end 306 can include a neck and a cap, and a septum 311 can be associated with the neck and cap 313. The plunger 308 can be formed from a plastic and/or rubber material such as, for example, an elastomeric polymer material. A liquid drug 310 can be contained between a sealing arrangement, including the septum 311, provided at the second end 306 of the drug container 302 and the plunger 308. The drug container 302 of the drug delivery device 100 can be a drug cartridge such as, for example, an ISO standardized drug cartridge.

The liquid drug 310 contained within the drug container 302 can be accessed through the second end 306 of the drug container 302. A drug container septum piercing mechanism 312 can be positioned at or near the second end 306 for accessing the liquid drug 310. The septum piercing mechanism 312 can access the liquid drug 310 through the septum 311. The septum piercing mechanism 312 can include a needle or other component to pierce the septum 311 to access the liquid drug 310. Prior to piercing the septum 311, the septum can remain unpierced and the liquid drug 310 inaccessible and sealed within the drug container 302. The septum piercing mechanism 312 can remain in an idle state prior to being activated to access the liquid drug 310. After activation, the needle of the septum piercing mechanism 312 can extend through the septum 311.

The septum piercing mechanism 312 can couple the liquid drug 310 to a needle conduit 314. The needle conduit 314 can include tubing (e.g., plastic tubing or metal tubing) and can provide a path for a portion of the liquid drug 310 that is expelled from the drug container 302. In various embodiments, the needle used to pierce the septum 311 can be a part of the needle conduit 314 as opposed to a portion of the drug container access mechanism 312.

In various embodiments, the septum piercing mechanism 312 can be positioned at or near the second end 306 along with the needle conduit 314. Thus, the liquid drug 310 stored in the drug container 302 can be accessed through the septum piercing mechanism 312 without having to move the drug container 302.

The needle conduit 314 can route the liquid drug 310 from the drug container 302 to a needle insertion mechanism or component 316. The needle insertion mechanism 316 can provide an entry point to a patient. The needle insertion mechanism 316 can include a hard needle and/or a soft needle or cannula that provides access to the patient such that the liquid drug 310 can be delivered to the patient.

The drug delivery device 100 can include a drive spring 318 and one or more force transfer elements 320. The force transfer elements 320 can be formed of any type of material including glass, metal (e.g., stainless steel), or a polymer or other plastic.

In an alternative embodiment, the drive spring 318 and the force transfer elements 320 can be used to expel the liquid drug 310 from the drug container 302. Specifically, the drive spring 318 can apply a force that can be applied to the force transfer elements 320. The force transfer elements 320 can be arranged to transfer the force from the drive spring 318 to the needle that pierces the septum 311. When the force from the drive spring 318 is applied to the septum piercing mechanism 312, a needle associated therewith can advance through the septum 311 (toward the first end 304). As the needle advances through the septum 311, the liquid drug 310 within the drug container 302 can be forced out of the drug container 302 into the needle conduit 314 and on to the needle insertion mechanism 316 for delivery to the patient.

The drive spring 318 can be any type of spring. The drive spring 318 can have any desired spring constant value, k. The drive spring 318 is not limited to a single spring and can include one or more springs. In various embodiments, the drive spring 318 can include one or more compression springs and/or torsion springs. For example, the drive spring 318 can include one or more linear compression springs arranged in a parallel arrangement, a series arrangement, an arrangement of nested springs in series, or any combination thereof. In various embodiments, the drive spring 318 can be implemented as double series springs.

The drive spring 318 can be directly coupled to the force transfer elements 320. In various embodiments, the drive spring 318 can include a fixed component or plate coupled to an end of the drive spring 318. The fixed component can have a width that is substantially the same as the width of the coils of the coils of the drive spring 318. The fixed component can be substantially flat and can be directly coupled to the force transfer elements 320.

The bottom portion 104 can include a track 324 for guiding the force transfer elements 320. The track 324 can be a guide, a tube, a housing or combinations thereof. In various embodiments, the drive spring 318 and the force transfer elements 320 can be positioned within the track 324. The track 324 can surround or cover the force transfer elements 320. The track 324 can be formed of any type of material including, for example, a plastic material or metal (e.g., stainless steel), or any combination thereof. For example, an outer portion of the curved portion of the track 324 may be formed of a metal while an inner portion of the curved portion of the track may before formed of a hard plastic. The track 324 can form any shape and can be arranged to take on any shape to guide the force transfer elements 320 from the drive spring 318 toward the cartridge 302.

Figure 5:
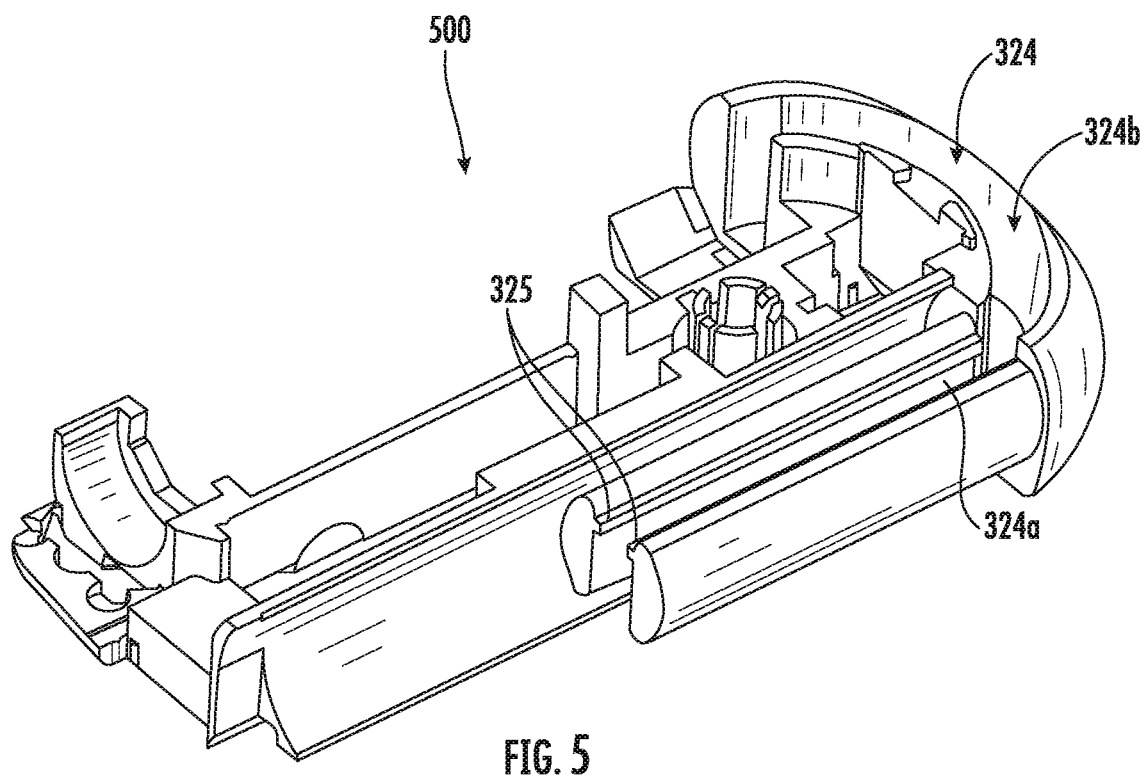
FIG. 5 illustrates an isometric view of an exemplary chassis for use with the drug delivery device of FIG. 1, in accordance with an embodiment of the present disclosure.
Figure 6:
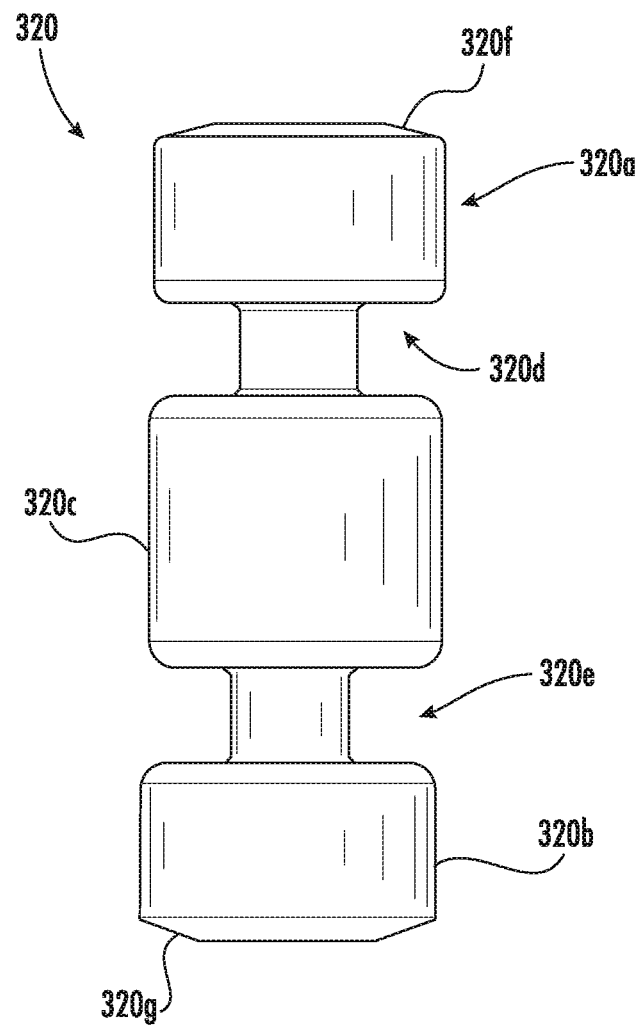
FIG. 6 illustrates a side view of an exemplary force transfer element for use with the drug delivery device of FIG. 1, in accordance with an embodiment of the present disclosure.

In various embodiments, the track 324 can have any cross-sectional shape. For example, the track 324 can have a circular cross-sectional shape. Overall, the track 324 can provide a desired arrangement and/or alignment of the transfer elements 320 relative to the drive spring 318 and the drug container 302. FIG. 5 shows an exemplary embodiment of a chassis 500 that includes at least a portion of the track 324, while FIG. 6 shows an exemplary force transfer element 320 having features to interact with the track.

The chassis 500 can include a variety of features for supporting the individual internal components of the drug delivery device 100. As mentioned, the chassis 500 may include the track 324 for guiding the force transfer elements 320. The track 324 may include a straight portion 324a and a curved portion 324b. The straight portion 324a of the track 324 may include first and second guide rails 325 disposed on opposite sides of the track. These first and second guide rails 325 may be sized and shaped to fit within corresponding grooves 320d/320e formed in the force transfer elements 320 (see FIG. 6) to maintain a desired orientation of the force transfer elements. The first and second guide rails 325 may also enhance the stiffness of the chassis 500 to prevent the straight portion 324a of the track 324 from splaying or separating under the forces associated with operation of the drug delivery device 100.

The force transfer elements 320 can be generally cylindrical, with top and bottom portions 320a, 320b and a central portion 320c. First and second grooves 320d, 320e may be located between the top and central portions 320a, 320c and the bottom and central portions 320b, 320c, respectively. The top and bottom portions 320a, 320b may include beveled upper/lower surfaces 320f, 320g to reduce the surface area that will contact surfaces of the track 324. One of the first and second reduced diameter portions 320d, 320e (depending on the orientation of the force transfer elements 320) may receive the first and second guide rails 325 of the track 324 to guide and support the cylindrical force transfer elements 320 within the straight portion of the track (e.g., where the spring 318 extends).

Referring again to FIGS. 3 and 4, prior to activation, the drive spring 318 can remain in an idle state. While in an idle state, the drive spring 318 can be compressed. When activated, the drive spring 318 can be allowed to expand. For example, after activation, the drive spring 318 can be allowed to expand to apply a force to that enables the drug container access mechanism 312 to cause a needle coupled to the needle conduit 314 to pierce the septum 311.

Once the septum 311 is pierced, the drug container 302 can be drained of its contents and delivered to a patient. The drive spring 318 and the force transfer elements 320 can be selected and adjusted to help regulate a flow of the liquid drug 310 from the drug container 302 to the needle insertion mechanism 316 based on a variety factors including the viscosity of the liquid drug 310.

In various embodiments, the drive spring 318 can be maintained in a compressed state prior to activation. Once activated, the drive spring 318 can be allowed to expand and apply a force to the one or more force transfer elements 320. An initial force provided by the drive spring 318 can cause the drug container access mechanism 312 to access the drug container 302. Specifically, the drug container access mechanism 312 can couple the liquid drug 310 to the needle conduit—for example, by forcing a needle of the needle conduit 314 to pierce the septum 311.

The drive mechanism of the drug delivery device 100 enables energy to be transferred in a different direction than the energy is initially provided. For example, the energy stored by the drive spring 318 can be transferred around a tight radius of curvature by the force transfer elements 320 (e.g., around a corner or 180 degrees from the where the energy is first directed as shown by the exemplary arrangement of the track 324). This enables the drug delivery device 100 to remain small and compact.

In general, the drug delivery device 100, and any other drug delivery device described herein, can generate a force in a first direction (e.g., the direction 330 based on the drive spring 318) and can apply the force in a second, opposite direction (e.g., the direction 340 based on the force transfer elements 320) to expel the liquid drug 310 from a drug container 302 in a precise and controlled manner. The direction 340 need not be opposite to the direction 330. That is, in various embodiments, the direction 340 of the force applied to the plunger 308 by the force transfer elements 320 can be in any direction relative to the direction 330 of the force provided by the drive spring 318. This enables the components of the drug delivery device 100 to be arranged in a close and tight manner, allowing the drug delivery device 100 to remain small and compact. In turn, the drug delivery device 100 can be more comfortable to wear and less cumbersome to the patient.

In various embodiments, the needle conduit 314 can be a needle formed from plastic or metal, or a combination thereof. An end of the need conduit 314 that can be coupled to the liquid drug 310 can be a hard end of the needle conduit 314 while the portion of the needle conduit 314 routed toward the needle mechanism 316 can be a soft portion of the needle conduit 314.

Figure 7:
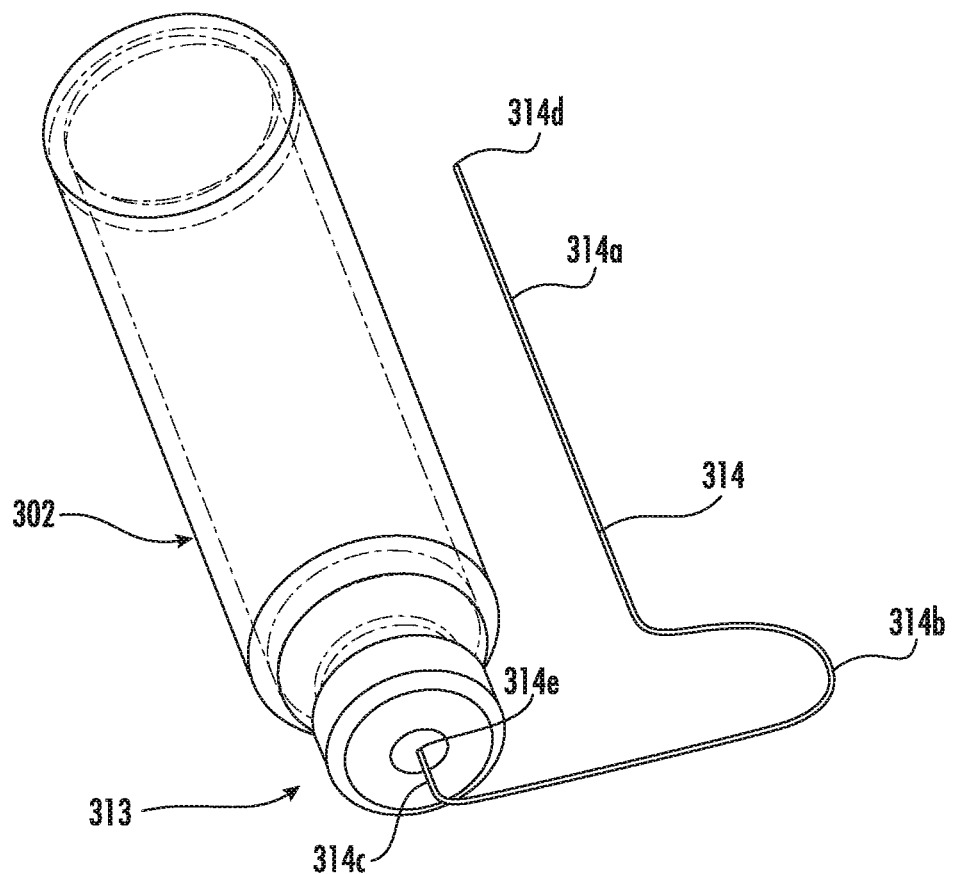
FIG. 7 illustrates an isometric view of a drug container and needle cannula portion of the drug delivery device of FIG. 1, in accordance with an embodiment of the present disclosure.

FIG. 7 shows an example of a drug container 302 provisionally engaged with a needle conduit 314 disposed within the septum (not shown) associated with the neck and cap 313 of the drug container. The needle conduit 314 is formed to have a straight portion 314a, a transverse U-shaped portion 314b, and a bent portion 314c. A distal end 314d of the straight portion 314a may be coupled to a cannula or needle (not shown) that will engage the patient. A distal end 314e of the bent portion 314c may be engaged with, or adjacent to, the septum (not shown) of the drug container 302. The disclosed arrangement of the needle conduit 314, particularly the transverse U-shaped portion 314b, can allow the conduit to flex during operation of the drug delivery device 100, for example, during the septum piercing operation, which requires the distal end 314e of the bent portion 314c to move with respect to the distal end 314d of the straight portion 314a. Desirably, this flexure occurs without yielding the needle conduit 314. Referring to FIGS. 3 and 4, the needle conduit 314 may be flexed to assume a slightly deformed shape upon fit-up with the rest of the components of the drug delivery device 100. Thus, the needle conduit 314 may be initially formed so that it resides in two dimensions (as shown in FIG. 7). In some embodiments the needle conduit 314 will be sterilized in this configuration. When the needle conduit is installed, however, it can assume a three-dimensional form when it is coupled to the septum piercing mechanism, needle insertion mechanism, chassis and top housing (as shown in FIGS. 3 and 4).

Figure 8:
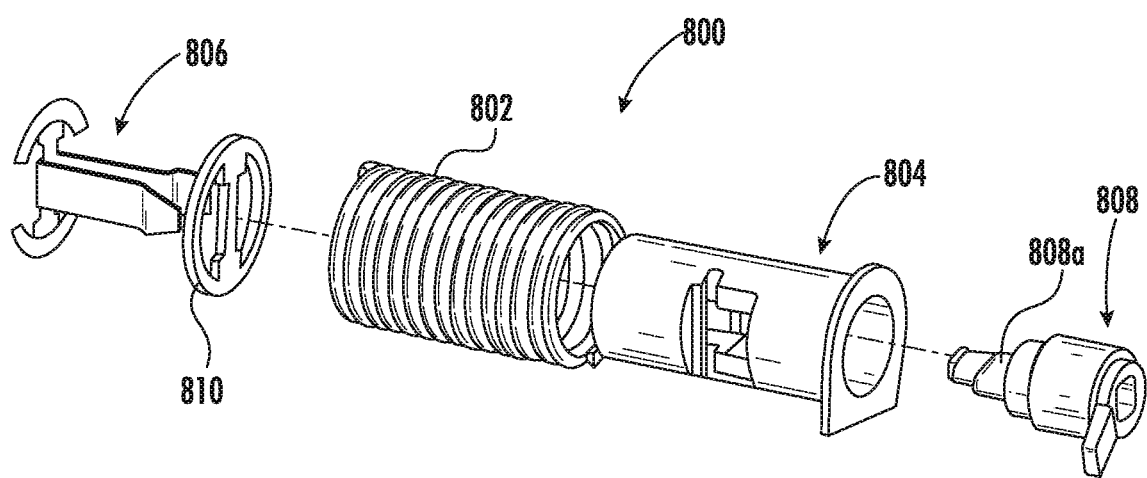
FIG. 8 illustrates an aspect of an exemplary drive system for use with the drug delivery device of FIG. 1, in accordance with an embodiment of the present disclosure.

FIGS. 8-11 illustrate views of an exemplary drive spring release mechanism 800 for us with the drug delivery device 100. In particular, FIG. 8 show an exemplary drive spring release mechanism 800 for use with the drug delivery device 100. As will be appreciated, the drive spring release mechanism 800 may retain the drive spring 802 in a compressed state until the user activates the drug delivery device to deliver the liquid drug to a patient. Upon activation, the drive spring release mechanism 800 releases the drive spring 802, allowing it to expand and press the force transfer elements into engagement with the plunger, which drives the plunger into the liquid drug container and expels the liquid drug through the needle conduit and needle.

Figure 9A:
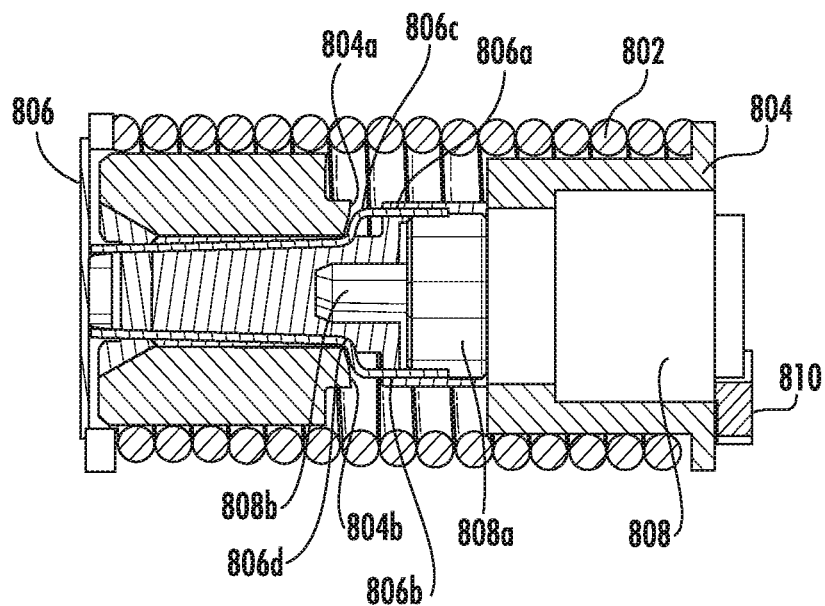
FIG. 9A illustrates a cross-sectional view of a drive spring release mechanism in a locked state, in accordance with an embodiment of the present disclosure.
Figure 9B:
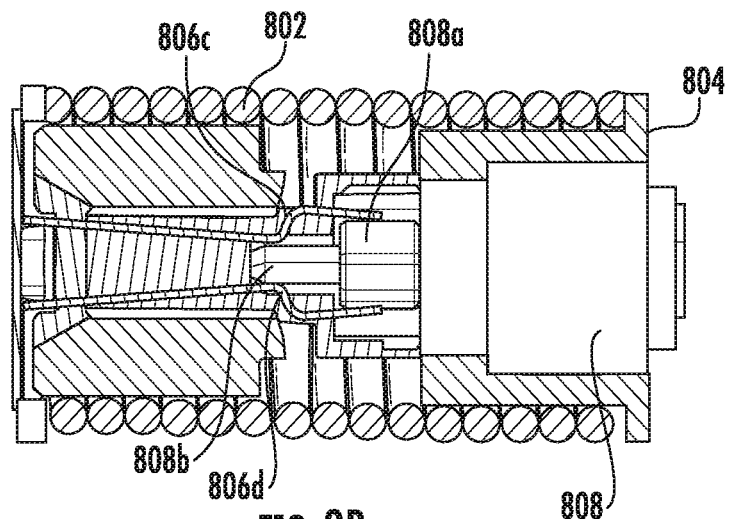
FIG. 9B illustrates a cross-sectional view of a drive spring release mechanism in an unlocked state, in accordance with an embodiment of the present disclosure.

The drive spring release mechanism 800 can include a drive spring 802, a drive mechanism lock 804, a spring retainer 806, a drive mechanism release 808, and a spring washer 810. The drive spring 802 can correspond to or represent the drive spring 318 depicted, for example, in FIGS. 3 and 4. FIGS. 9A and 9B illustrate cross-sectional views of the drive spring release mechanism 800 in a locked state, and an unlocked state, respectively.

Advantageously, the disclosed spring release mechanism 800 enables the drive spring 802 to be compressed outside of drug delivery device during manufacture. It also allows for testing of the drive spring 802 externally from the device during assembly. The spring retention mechanism is configured to retain the high spring force of the drive spring 802 without loading the chassis or other enclosure parts. The drive spring 802 is locked in a compressed state and is retained by the release mechanism. The spring release mechanism is activated by the needle mechanism via an appropriate linkage engaging the spring release mechanism 800 via the drive mechanism release 808.

FIG. 9A shows the drive spring release mechanism 800 in a locked state with the drive spring 802 in a compressed state. In this configuration, the drive mechanism lock 804 and the spring retainer 806 capture the drive spring 802 at opposite ends of the spring to prevent the compressed spring from expanding. The spring retainer 806 can have first and second longitudinally extending spring arms 806a, 806b, which extend to engage a cam surface 808a of the drive mechanism release 808. In the locked state, the cam surface 808a forces distal ends of the spring arms 806a, 806b outward so that portions 806c, 806d of the distal ends engage associated stop surfaces 804a, 804b of the drive mechanism lock 804. The portions 806c, 806d are a jog from a substantially longitudinal direction, to a substantially radial direction, and finally to a substantially longitudinal direction. The jog is the short portions 806c, 806d of the spring arms 806a, 806b that transition between two different sections that are offset radially. The portion of the jog in the substantially radial direction engages the stop surfaces 804a, 804b of the drive mechanism lock 804 in the locked state. As will be appreciated, since the drive spring 802 is in a compressed state, it exerts a biasing force against the drive mechanism lock 804 and the spring retainer 806, tending to force them apart. The interengagement of the stop surfaces 804a, 804b and the spring arms 806a, 806b prevents the distal ends of the spring arms from moving longitudinally (i.e., along the longitudinal axis of the drive spring 802), thereby locking the spring retainer 806 to the drive mechanism lock 804, and maintaining the drive spring in a compressed state. The cam surface 808a may be operated by radial translation of a radially extending arm 810 of the drive mechanism lock. A cam extension 808b extends longitudinally from the drive mechanism release 808 and has a width less than a distance between the arms 806a, 806b in the unlocked state. The cam extension 808b allows the drive mechanism release 808 to align with the spring retainer 806 and is thin enough to spread apart the arms 806a, 806b for insertion of the cam surface 808a.

FIG. 9B shows the drive spring release mechanism 800 in an unlocked state. In this state, the drive spring release mechanism 800 has been rotated from its position in the locked state, so that the cam surface 808a no longer forces the distal ends of the spring arms 806a, 806b outward sufficiently to engage associated stop surfaces 804a, 804b of the drive mechanism lock 804. Rather, in the illustrated unlocked state, the spring arms 806a, 806b, which may be manufactured to be naturally biased inward, release toward each other such that the distal ends of the spring arms clear the stop surfaces 804a, 804b of the drive mechanism lock 804. The lack of interengagement between the stop surfaces 804a, 804b and the spring arms 806a, 806b allows the distal ends of the spring arms to move longitudinally (i.e., along the longitudinal axis of the drive spring 802), thereby releasing the drive spring 802 so that it can expand. This, in turn, allows the drive spring 802 to push the spring retainer 806 down the track 324, pushing the force transmitting elements 320 into the liquid drug container 302 and dispensing the liquid drug 310 contained in the liquid drug container.

Figure 9C:
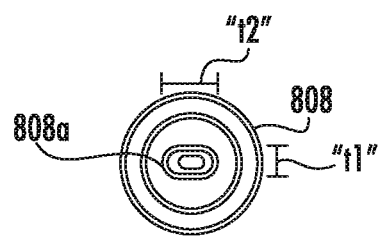
FIG. 9C illustrates a left end view of the drive spring release mechanism of FIG. 9B, in accordance with an embodiment of the present disclosure.

As mentioned, the spring drive release mechanism 800 may lock or unlock the drive spring 802 depending on the rotational orientation of the cam surface 808a of the drive mechanism release 808. As shown in FIG. 9C, which is an end view of the spring drive release mechanism 800, the cam surface 808a may have an oval shape so that in a first rotational orientation it may have a first thickness "t1" and in a second rotational orientation it may have a second thickness "t2" which is different from the first thickness. The thicknesses "t1" and "t2" may be selected to provide a desired operability to the spring drive release mechanism. Thus arranged, the spring drive release mechanism 800 may be locked or unlocked depending upon the rotational orientation of the drive mechanism release 808. For example, in the orientation shown in FIG. 9C the cam surface 808a presents thickness t1 to the distal ends of the spring arms 806a, 806b of the spring retainer 806. This allows the distal ends of the spring arms 806a, 806b to flex inward and out of engagement with the stop surfaces 804a, 804b of the drive mechanism lock 804 (i.e., the unlocked configuration of FIG. 9B). When the cam surface 808a is rotated 90-degrees from the position shown in FIG. 9C, the cam surface 808a presents larger thickness t2 to the distal ends of the spring arms 806a, 806b of the spring retainer 806. This presses the distal ends of the spring arms 806a, 806b outward into engagement with the stop surfaces 804a, 804b of the drive mechanism lock 804 (i.e., the locked configuration of FIG. 9A).

Figure 10A:
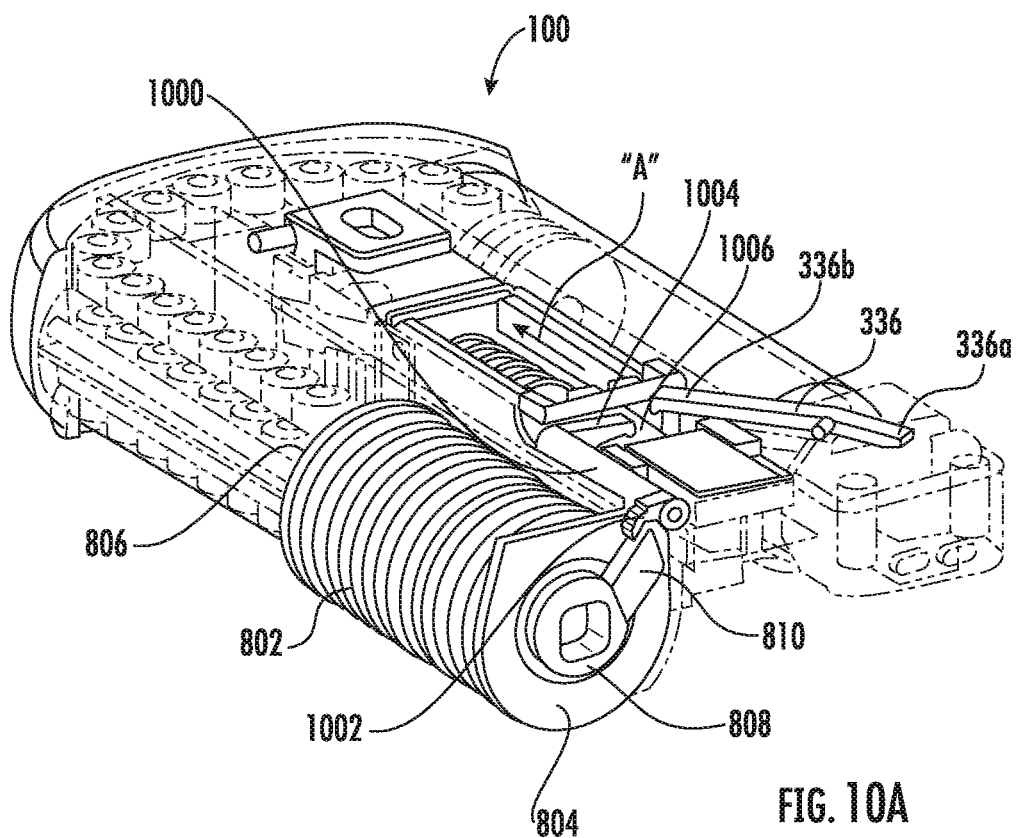
FIG. 10A illustrates an isometric view of a drive system in a locked state, in accordance with an embodiment of the present disclosure.
Figure 10B:
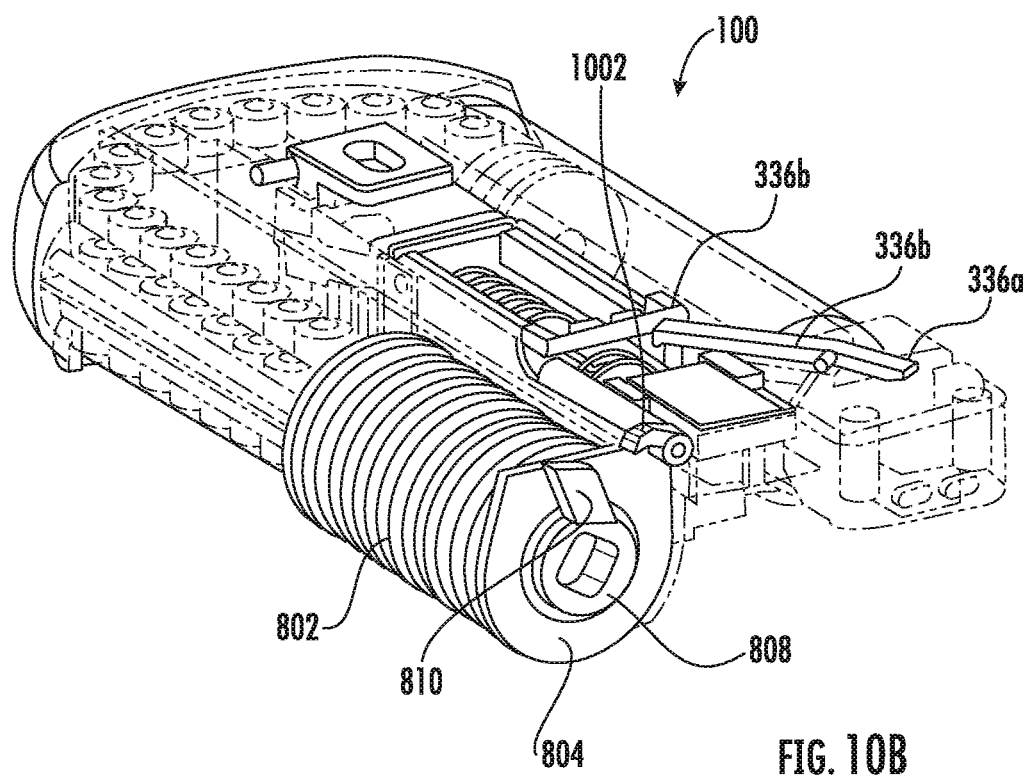
FIG. 10B illustrates an isometric view of a drive system in an unlocked state, in accordance with an embodiment of the present disclosure.

The spring drive release mechanism 800 may be from a locked state to an unlocked state, as mentioned, by rotating the drive mechanism release 808. FIG. 10A shows the drug delivery device 100 with the spring drive release mechanism 800 in the locked configuration of FIG. 9A. FIG. 10B shows the drive system in an unlocked state. As can be seen, a pivotable drive lock 1000 has a first arm 1002 at a first end that is engageable with a radially extending arm 810 of the drive mechanism lock 800. The pivotable drive lock 1000 has a second arm 1004 at a second end that is engageable with a needle insert mechanism 1006. When the drug delivery device is activated, the needle insert mechanism 1006 is moved away from the second arm 1004 (along the direction of arrow "A"). A needle retract mechanism 1008 (an isometric and top view of a drive system in FIG. 11) also moves in the direction of arrow "A" during the needle insertion operation, and then retracts (in the direction opposite of arrow "A") after the needle and a soft cannula (not shown) are inserted. During the needle insertion operation, the needle insert and needle retract mechanisms 1006, 1008 prevent the second arm 1004 from moving. Once the needle retract mechanism 1008 has fully retracted, however, it no longer maintains contact with the second arm, such that the second arm 1004 can move downward. This rotates the pivotable drive lock 1000 so that the first arm 1002 rotates out of engagement with the radially extending arm 810 of the drive mechanism release 808.

Figure 10C:
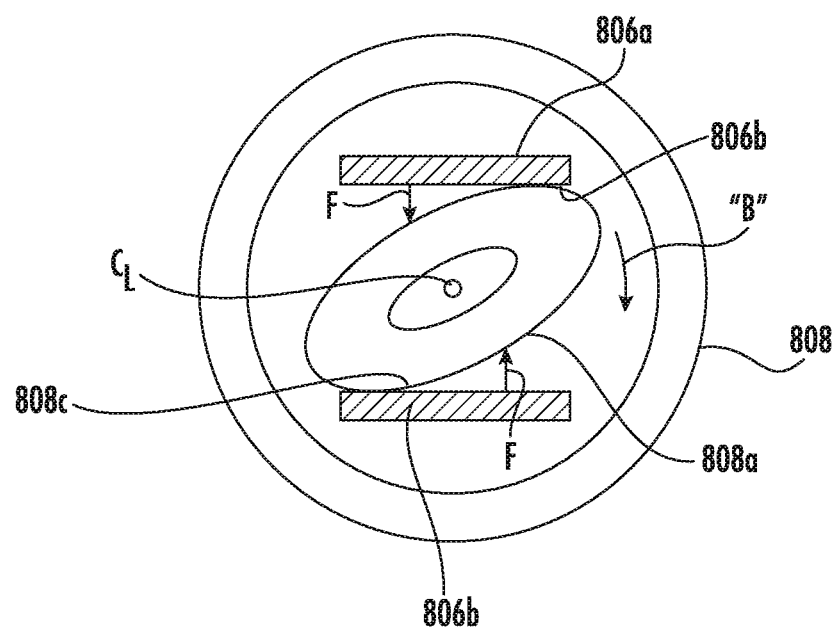
FIG. 10C illustrates left view of a drive mechanism release in a locked state, in accordance with an embodiment of the present disclosure.

Once the radially extending arm 810 is free from the constraint of the first arm 1002, the expansion force of the drive spring 802 can be employed to rotate the drive spring release mechanism 800 from the locked configuration (FIG. 9A) to the unlocked configuration (FIG. 9B). As shown in FIG. 10C, in the locked configuration the drive mechanism release 808 can be rotationally positioned such that the distal ends of the spring arms 806a, 806b of the spring retainer 806 engage the cam surface 808a at first and second positions 808b, 808c that are radially offset from the rotational centerline CL of the drive release mechanism 808. As previously noted, the spring arms 806a, 806b may be naturally biased toward each other. Due to the offset-engagement arrangement between the spring arms 806a, 806b and the cam surface 808a, this biasing will tend to rotate the cam surface 808a in the direction of arrow "B," thus positioning the drive mechanism release in the configuration of FIG. 9B. This biasing may be further aided by the expansion force of the drive spring 802, which, when allowed to expand causes the spring retainer 806 to move away from the drive mechanism lock 804. This causes the distal ends of the spring arms 806a, 806b of the spring retainer 806 to engage the stop surfaces 804a, 804b of the drive mechanism lock 804. In some embodiments, the stop surfaces 804a, 804b and the distal ends of the spring arms 806a, 806b may have complimentary angled surfaces so that when the stop surfaces engage the spring arms they force the spring arms together. This, in turn, places additional force "F" on the cam surface 808a, causing it to rotate in the direction of arrow "B," and positioning the drive mechanism 808 release in the configuration of FIG. 9B.

The rotated (i.e., unlocked) configuration of the spring drive release mechanism 800 is shown in FIG. 10B, and corresponds to the configuration of FIG. 9B. The locked configuration of the spring drive release mechanism 800 is shown in FIG. 10A, and corresponds to the configuration of FIG. 9A.

The drive mechanism release 808 may have a second cam surface, disposed longitudinally outward from the cam surface 808a. This second cam surface may have dimensions that are smaller than the outer dimensions of the cam surface. The second cam surface may be used to assist in moving the spring arms 806a, 806b outward, away from each other, during initial locking of the spring drive release mechanism. Thus, when the drive spring 802 is initially compressed during manufacture of the drug delivery device 100, the drive mechanism release may be rotated so that the second cam surface engages the spring arms 806a, 806b apart by an amount sufficient that the cam surface 808a can then fully engage the spring arms to drive them fully outward and into engagement with the stop surfaces 804a, 804b of the drive mechanism lock 804. In some embodiments, the second cam surface has an oval shape in cross section, similar to, but smaller than, the oval cross section of the cam surface 808a.

The compressed drive spring 802 can be assembled in the spring drive release mechanism 800, which can then be assembled to the chassis as a unit. The spring drive release mechanism 800 can engage a drive interlock to hold the spring in a locked state. Once the needle mechanism has been actuated (insert and retract) the drive interlock releases the spring drive release mechanism 800 to activate the drive spring 802.

Figure 12:
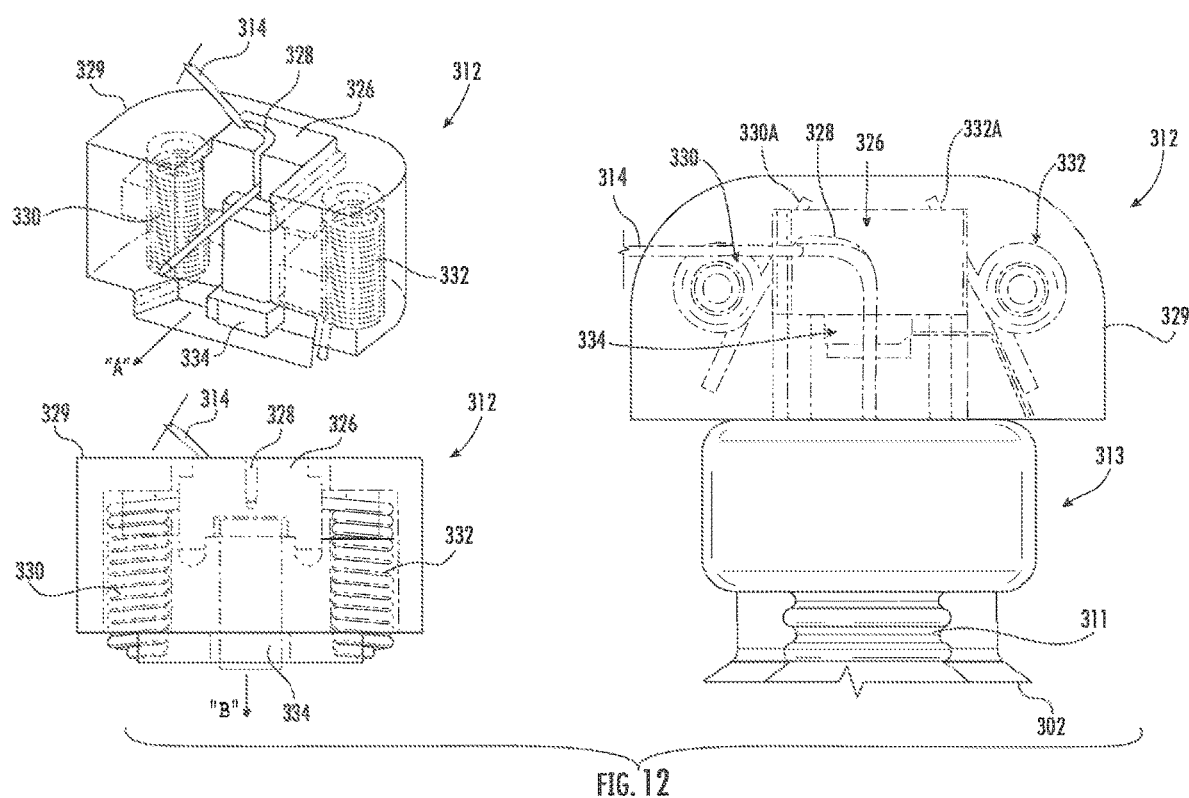
FIG. 12 illustrates aspects of an exemplary cartridge septum piercing arrangement for use with the drug delivery device of FIG. 1, in accordance with an embodiment of the present disclosure.

In an unactivated state, the end of the needle conduit 314 is separated from the liquid drug 310 in the liquid drug container 302 by a septum 311. Activation of the drug delivery device 100 can activate a septum piercing mechanism 312 that pierces the septum 311 of the liquid drug container 302 to couple the liquid drug 310 to the needle conduit 314. FIG. 12 illustrates an exemplary septum piercing mechanism 312 that can be activated when the drug delivery device 100 is activated.

The septum piercing mechanism 312 may be mounted adjacent to the neck and cap 313 of the liquid drug container 302. The septum piercing mechanism 312 may include a needle slider 326 that guides and supports the needle cannula 314 to press a distal end (not shown) of the needle cannula through the septum 311 of the liquid drug container 302 to couple the liquid drug 310 to the needle conduit 314. The needle slider 326 may include a guide channel 328 which receives the needle conduit 314. The guide channel 328 may include a 90-degree bend that conforms to the geometry of the received needle conduit 314.

Figure 11:
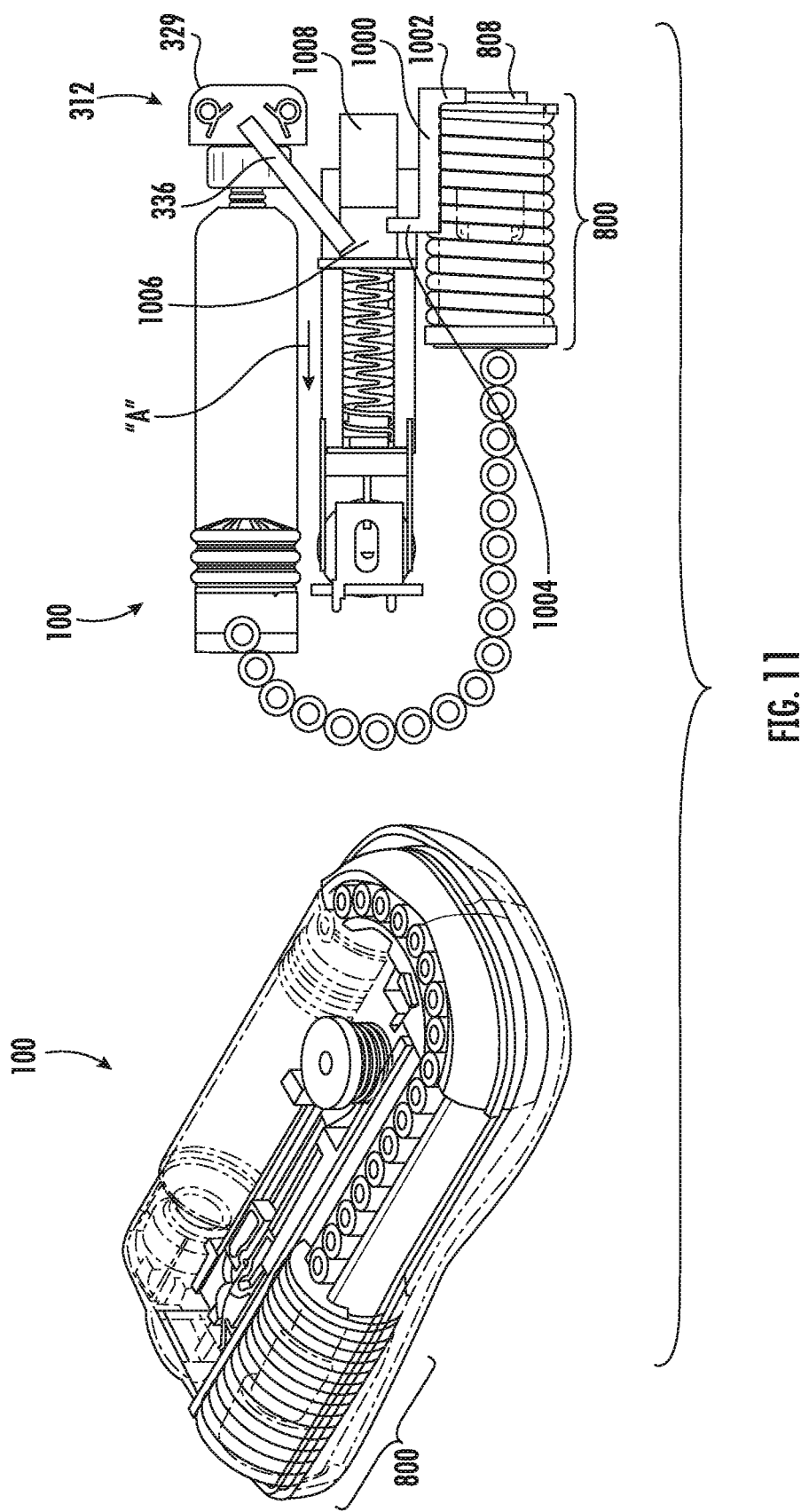
FIG. 11 illustrates an isometric and top view of a drive system, in accordance with an embodiment of the present disclosure.

The needle slider 326 may be guided for movement in a guide track 329, which may be coupled to the bottom portion 104 of the drug delivery device 100. The guide track 329 may also house first and second torsion springs 330, 332 having first and second legs 330A, 332A, which bear against a rear surface of the needle slider 326, biasing it toward the drug container 302 (i.e., in the direction of arrow "A"). A trigger lock 334 engages the needle slider 326 to prevent the needle slider 326 (and needle conduit 314) from moving until the drug delivery device 100 is activated. The trigger lock 334, in turn, is supported by a trigger lever 336 (FIGS. 10A, 10B and 11), which holds the trigger lock in place until the drug delivery device 100 is activated. The trigger lever 336 has a first end 336a that engages the trigger lock 334, and a second end 336b that engages the needle insert mechanism 1006 (FIGS. 10A and 11). When the drug delivery device is in the unactivated configuration, the needle insert mechanism 1006 prevents the trigger lever 336 (and thus the trigger lock 334) from moving. When the drug delivery device 100 is activated, the needle insert mechanism 1006 (and needle retract mechanism 1008) operate in the manner previously described, moving away from the trigger lever 336 and allowing it to pivot such that the first end 336a of the trigger lever no longer maintains the trigger lock 334 in place. The trigger lock 334 thus moves in the direction of arrow "B," allowing the needle slider 326 and the needle cannula 314 to move in the direction of arrow "A" under the force of the first and second torsion springs 330, 332, until the end of the needle conduit pierces the septum 311 within the drug container, exposing the needle conduit to the liquid drug within the drug container.

Figure 13:
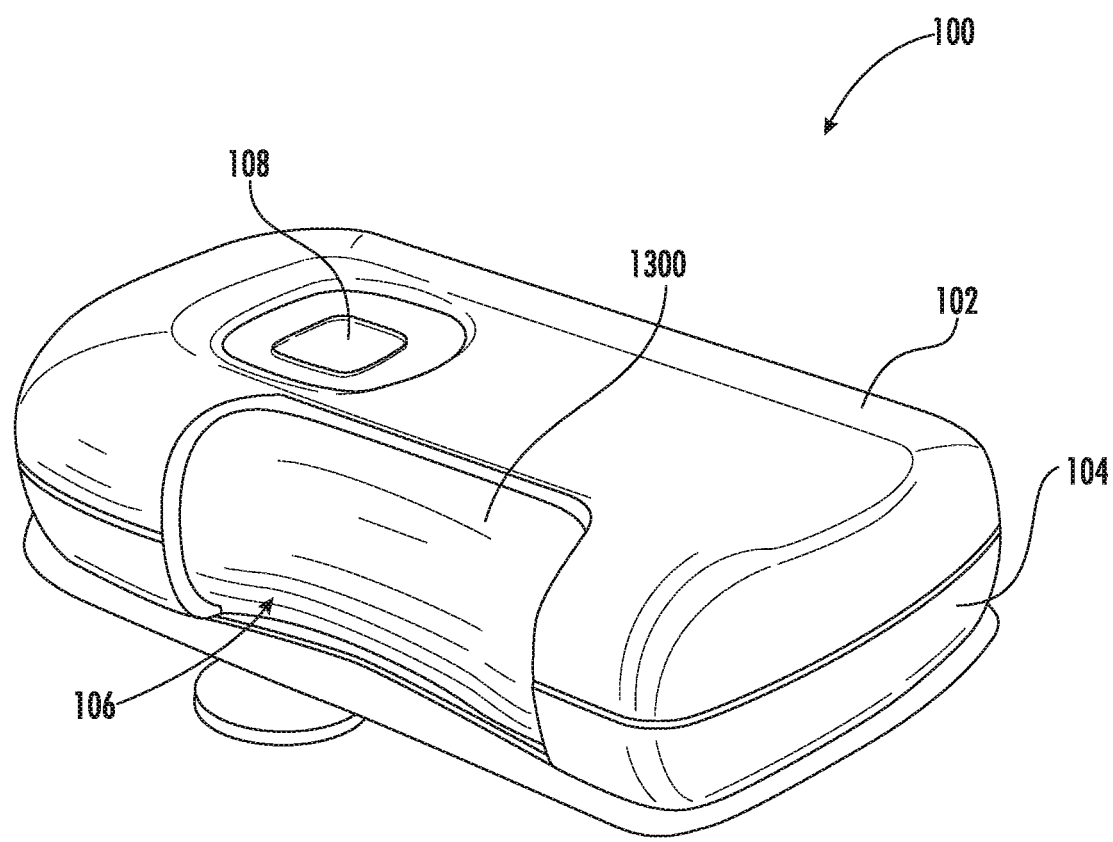
FIG. 13 illustrates an aspect of an exemplary case portion of the drug delivery device of FIG. 1.
Figure 14A:
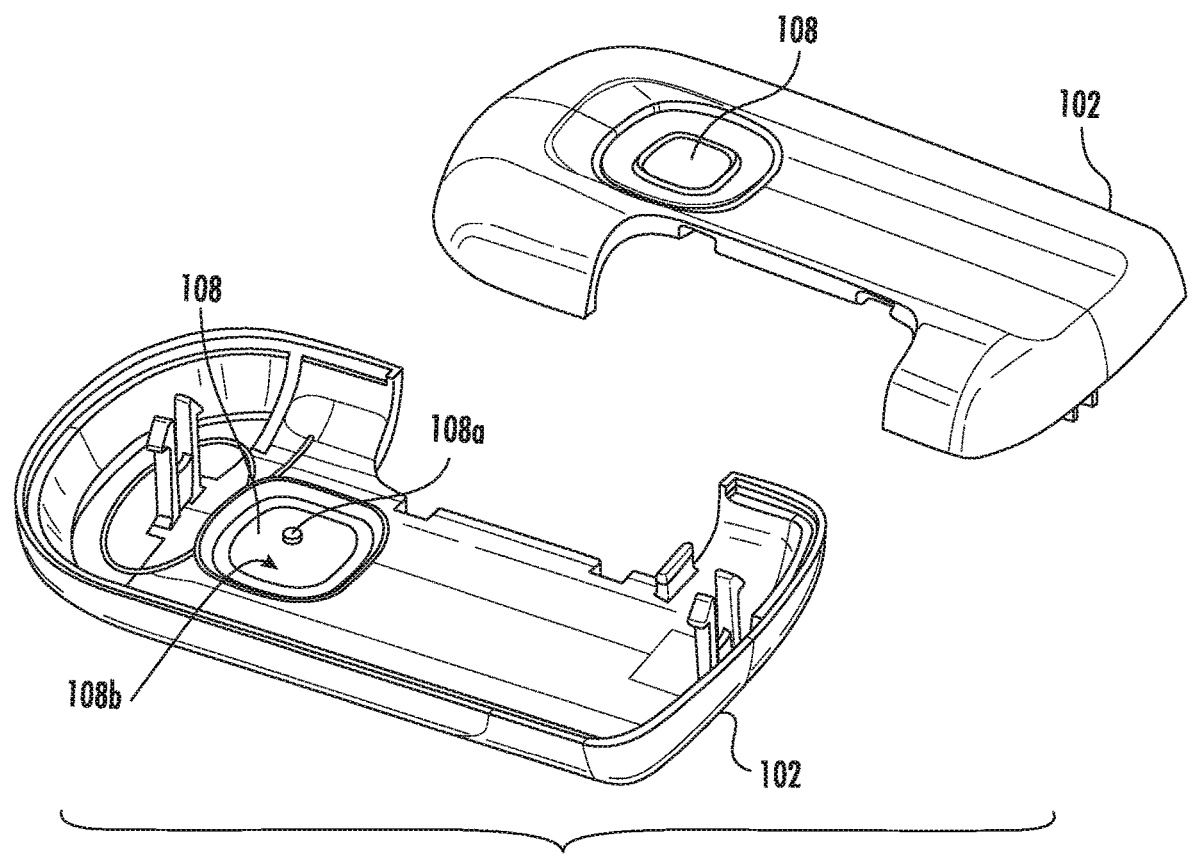
FIG. 14A illustrates a isometric view of a button lock structure of an aspect of an exemplary case portion of the drug delivery device of FIG. 1.
Figure 14B:
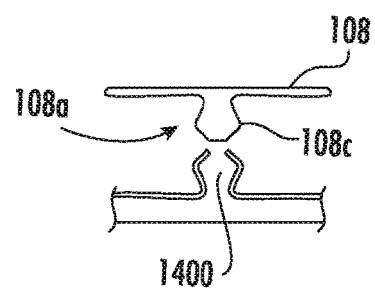
FIG. 14B illustrates a cross-section of a button lock structure of an aspect of an exemplary case portion of the drug delivery device of FIG. 1.
Figure 15:
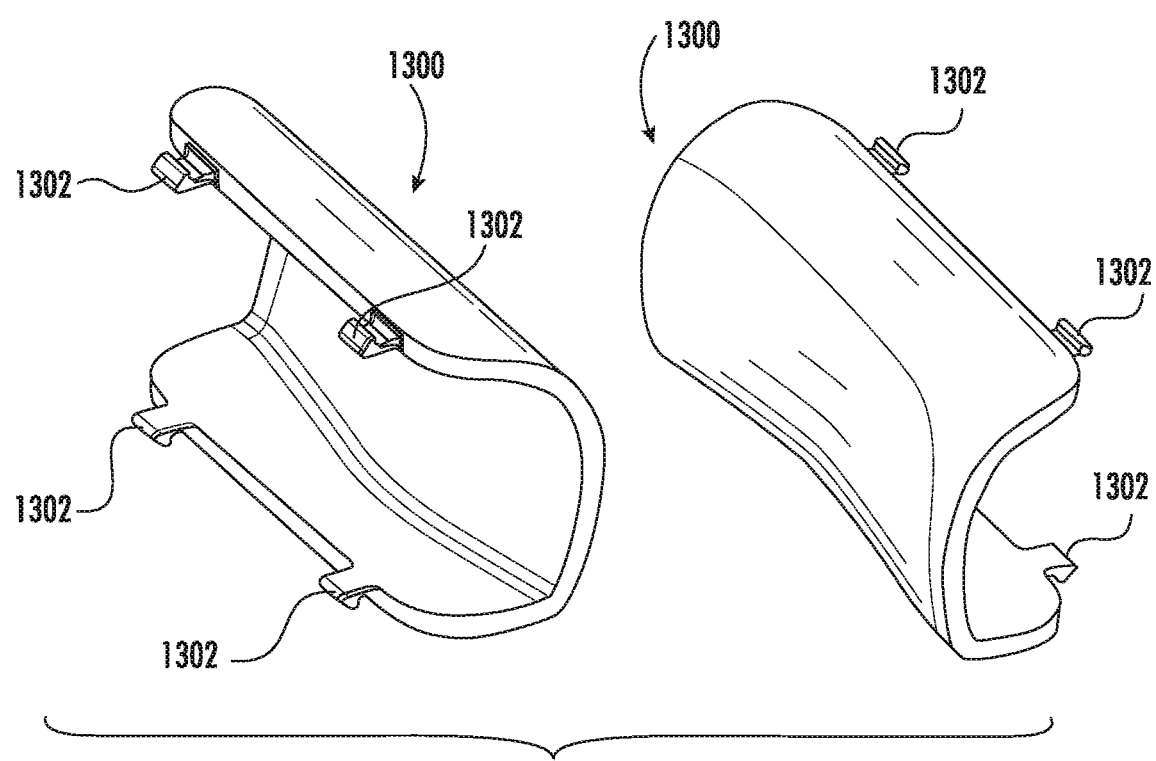
FIG. 15 illustrates an aspect of an exemplary case portion of the drug delivery device of FIG. 1.

FIGS. 13-15 describe embodiments of the user activation element 108 and cover 1300 that can be provided over opening 106 in the drug delivery device top portion 102 and/or bottom portion 104. In particular, FIG. 13 illustrates an isometric view of an aspect of an exemplary case portion of a drug delivery device. FIGS. 14A and 14B illustrate an isometric and a cross-sectional view of a button lock structure of an aspect of an exemplary case portion of a drug delivery device. The user activation element 108 may be an elastomeric button that, when pressed, interacts with components within the drug delivery device 100 to deliver liquid drug 310 from the liquid drug container 302 to the user via the needle. In some embodiments, the user activation element 108 may have a tactile feature that affirms to the user that the device has been activated. The user activation element 108 may have a protrusion 108a disposed on an interior-facing portion 108b of the user activation element. This protrusion 108 may include an expanded diameter portion 108c that can interact with a recess 1400 associated with a button lock structure within the drug delivery device 100 so that, when the user activation element 108 is depressed, the recess captures the expanded diameter portion so that the user activation element remains depressed. This retention feature can, as mentioned, provide the user with feedback that the device has been activated.

FIG. 15 shows a viewing window element 1300 for covering the opening 106 in the casing of the drug delivery device 100. As previously mentioned, the opening 106 may be disposed directly adjacent to the liquid drug container 302 so that a user can view the status of the container (i.e., the user can tell whether all the liquid drug 310 has been expelled from the container). Thus, in some embodiments the viewing window element 1300 is sufficiently transparent for the user to determine the evacuation status of the liquid drug container through naked eye observation of the position of the plunger 308 (FIG. 3). As can be seen, the viewing window element 1300 has a C-shape which enables it to wrap around the top and bottom portions 102, 104 of the device case. This C-shape allows the user to view the drug container 302 (and the plunger 308) from a variety of different angles and positions. This enables the user to wear the device 100 in a variety of positions on the body (thigh, waist, etc.) while still being able to view the drug container 302 and plunger 308 easily.

In the illustrated embodiment, the viewing window element 1300 is provided with a plurality of snaps 1302 at upper and lower portions of the element. These snaps 1302 are configured to engage corresponding recesses or other features in the top and bottom portions 102, 104. It will be appreciated, however, that a snap-fit arrangement is not critical, and that the viewing window element 1300 can be coupled to the top and bottom portions 102, 104 of the device 100 in any of a variety of ways, including press-fit, adhesive, welding, integral molding, and the like.

Referring now to FIGS. 16-23, a sterilization system for use with portions of the drug delivery device will be described. As will be understood, it is desirable that portions of the drug delivery device that will be exposed to liquid drug 310 be sterilized.

Figure 16:
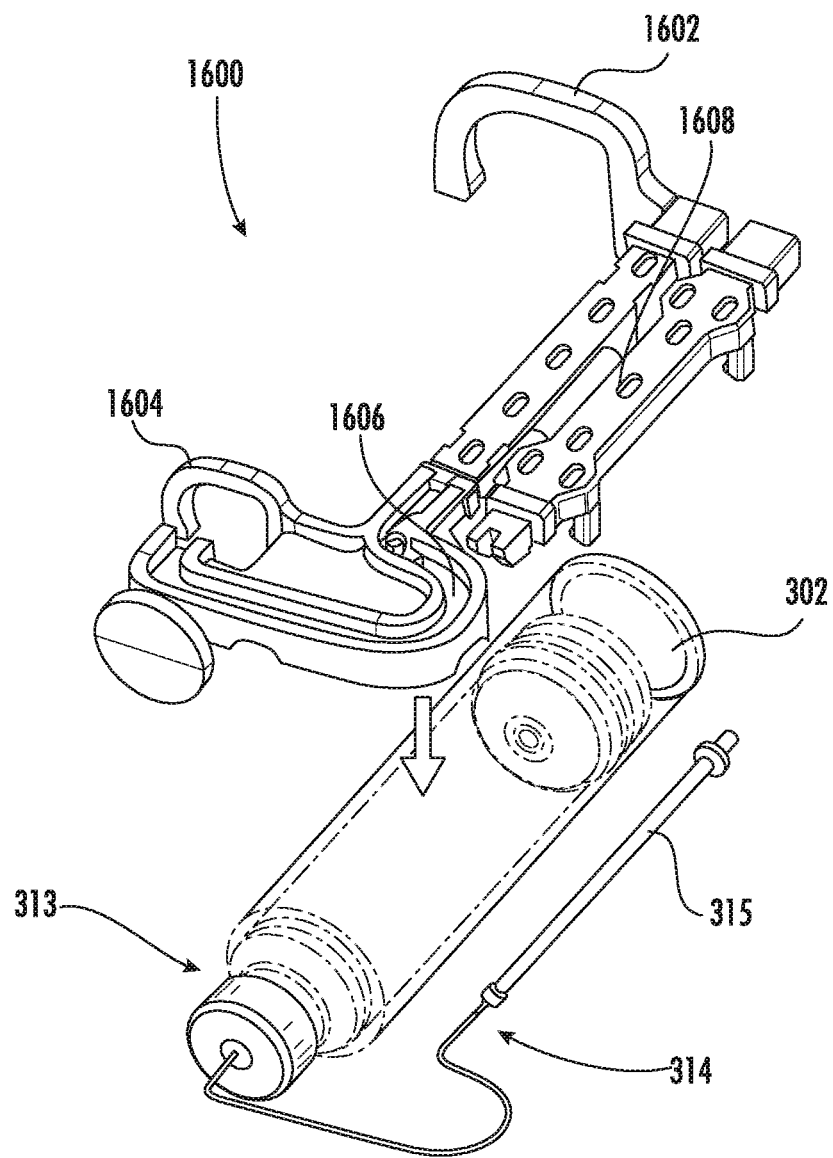
FIG. 16 illustrates an aspect of an exemplary carrier device for use in sterilizing the cartridge and needle cannula portion of a drug delivery device, in accordance with an embodiment of the present disclosure.
Figure 17:
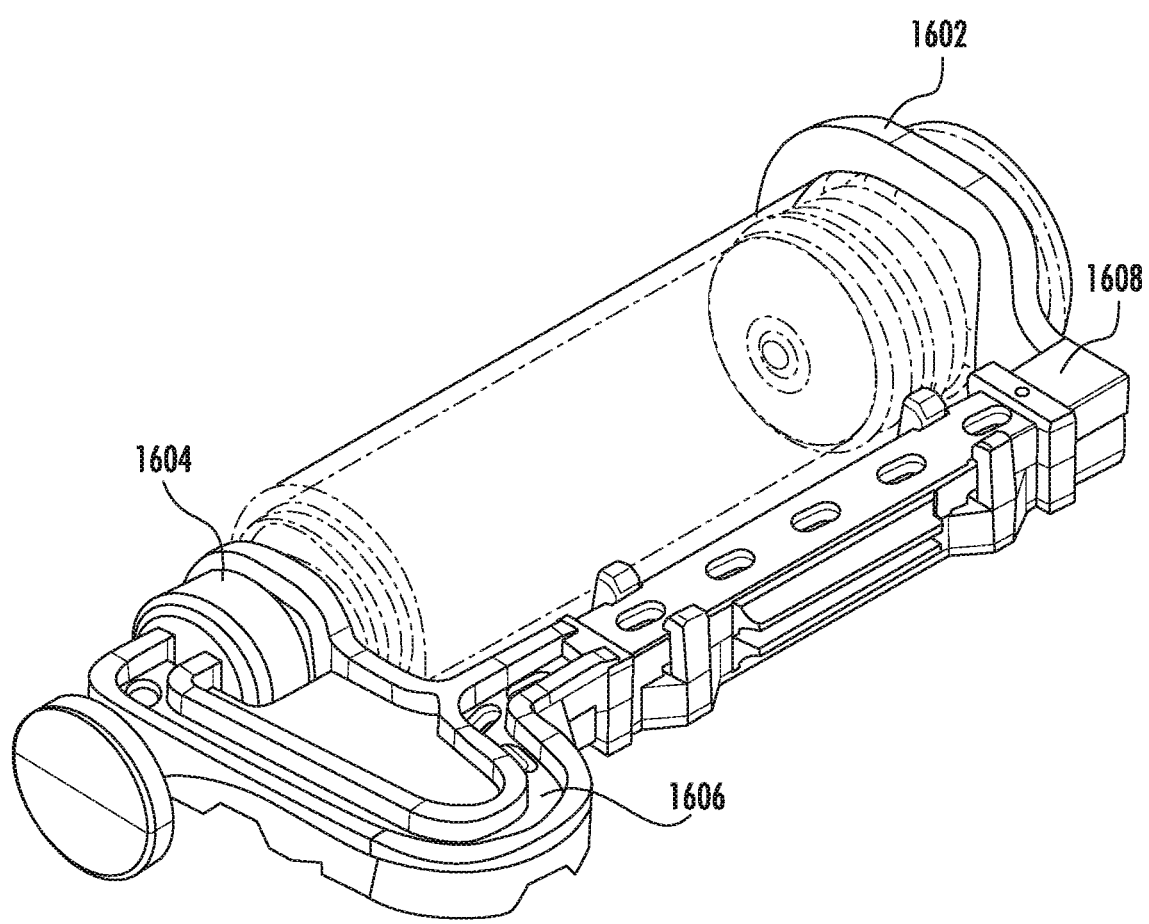
FIG. 17 illustrates an aspect of an exemplary carrier device for use in sterilizing the cartridge and needle cannula portion of a drug delivery device, in accordance with an embodiment of the present disclosure.
Figure 18:
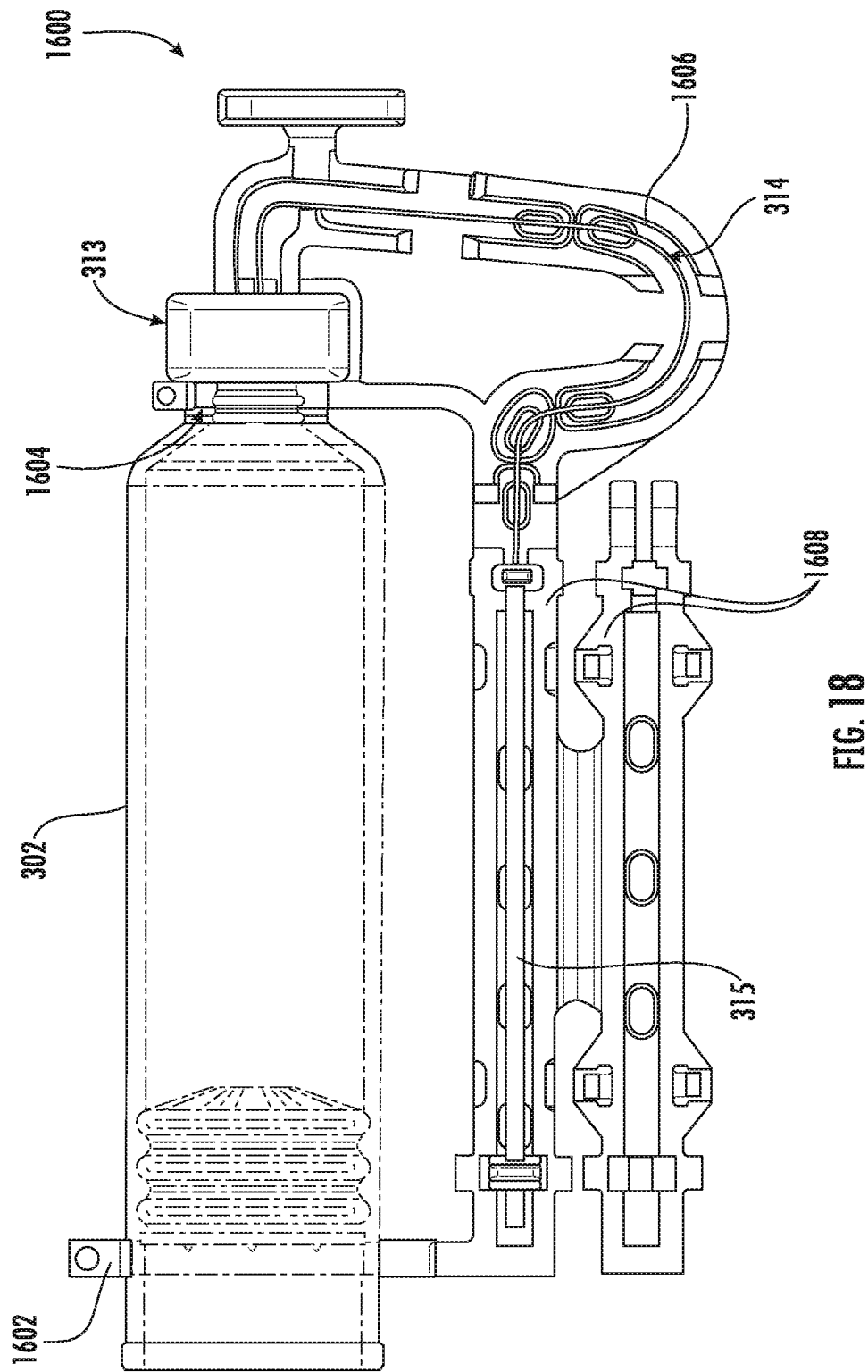
FIG. 18 illustrates an aspect of an exemplary carrier device for use in sterilizing the cartridge and needle cannula portion of a drug delivery device, in accordance with an embodiment of the present disclosure.
Figure 19:
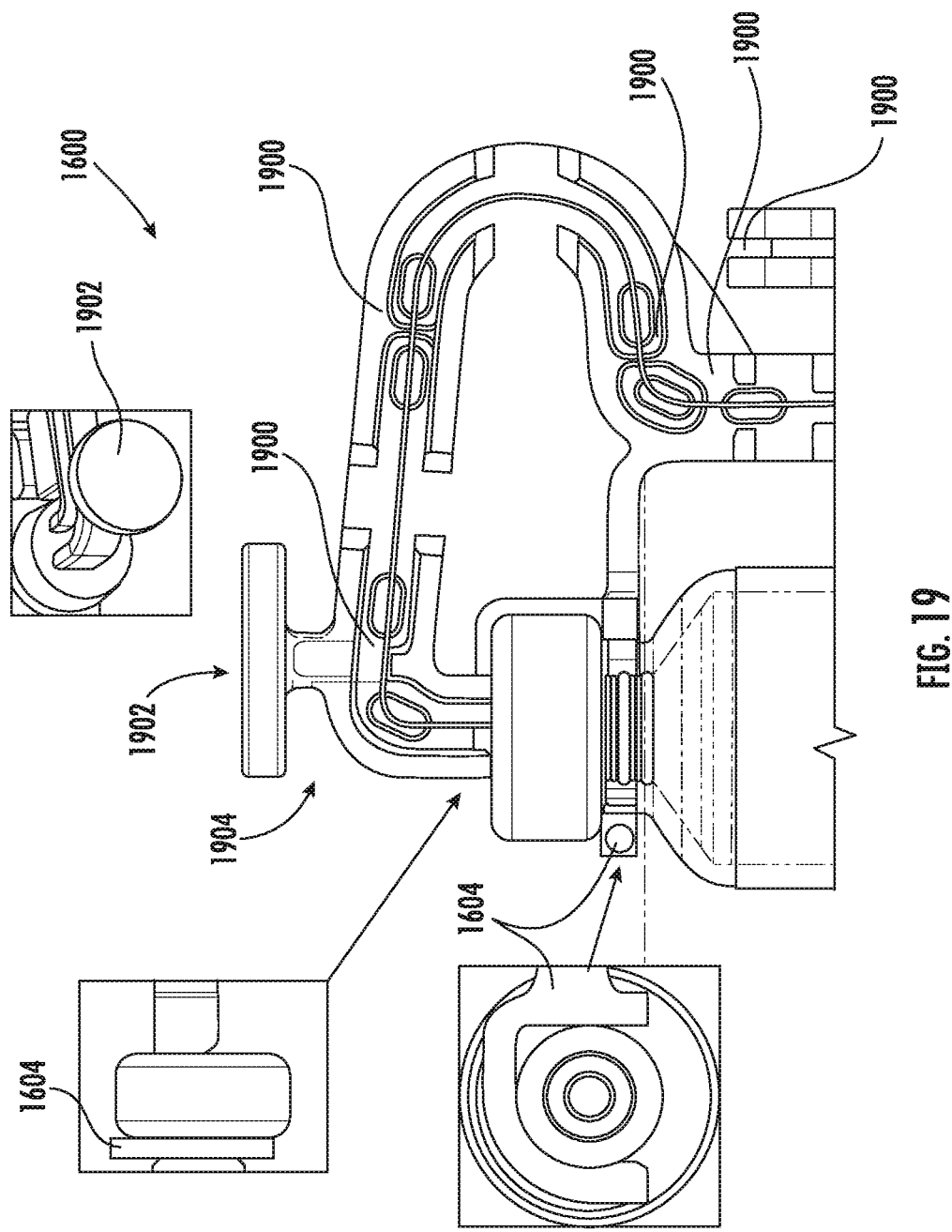
FIG. 19 illustrates an aspect of an exemplary carrier device for use in sterilizing the cartridge and needle cannula portion of a drug delivery device, in accordance with an embodiment of the present disclosure.

FIGS. 16 and 17 shows an exemplary carrier 1600 for engaging the liquid drug container 302, neck and cap 313, needle conduit 314, soft cannula (not shown), and a sterile barrier 315 used to maintain sterility of the needle conduit and other components (collectively referred to as a "fluid path"). As will be discussed, the carrier 1600 may hold these elements and may interface with other sterilization system components to facilitate efficient sterilization of multiple units at one time. The disclosed carrier 1600 may enable a pre-assembled liquid drug container 302 with attached fluid path (needle conduit 314, sterile barrier 315) to go through fill finish and sterilization process The carrier 1600 may have a cylinder-engaging portion 1602, a neck-engaging portion 1604, a needle conduit-engaging portion 1606 and a sterile barrier-engaging portion 1608. Some or all portions may be configured to snap-fit to the respective system elements. FIG. 18 illustrates in detail the manner in which the carrier 1600 engages and houses the liquid drug container 302, neck and cap 313, needle conduit 314 and sterile barrier 315. As can be seen, the portion of the carrier 1600 that covers/encapsulates the sterile barrier 315 may be formed in two halves, like a clamshell that can be closed around the sterile barrier. FIG. 19 illustrates the engagement features for holding the needle conduit 314 within the carrier 1600. Specifically, individual crush-features 1900 are disposed at a plurality of locations along the length of the needle conduit 314, and serve to gently hold the needle conduit in place against the carrier 1600. The crush-features 1900 may each form a recess that is slightly smaller than the diameter of the needle conduit 214 to hold the conduit in an interference fit. A weighing feature 1902 may be provided at one end 1904 of the carrier 1600, which is at the radial center of gravity of the carrier when loaded with a drug container. The feature 1902 allows the carrier 1600 to stand in an upright configuration with the feature 1902 providing one point of contact with a foundation (e.g., a table surface, a scale, or the like). With the carrier 1600 balanced in an upright position using the feature 1902, the drug container may be filled with a fluid while standing on a scale. When a certain weight is measured from the scale, the supply of fluid to the drug container may cease to provide fill accuracy.

Figure 20:
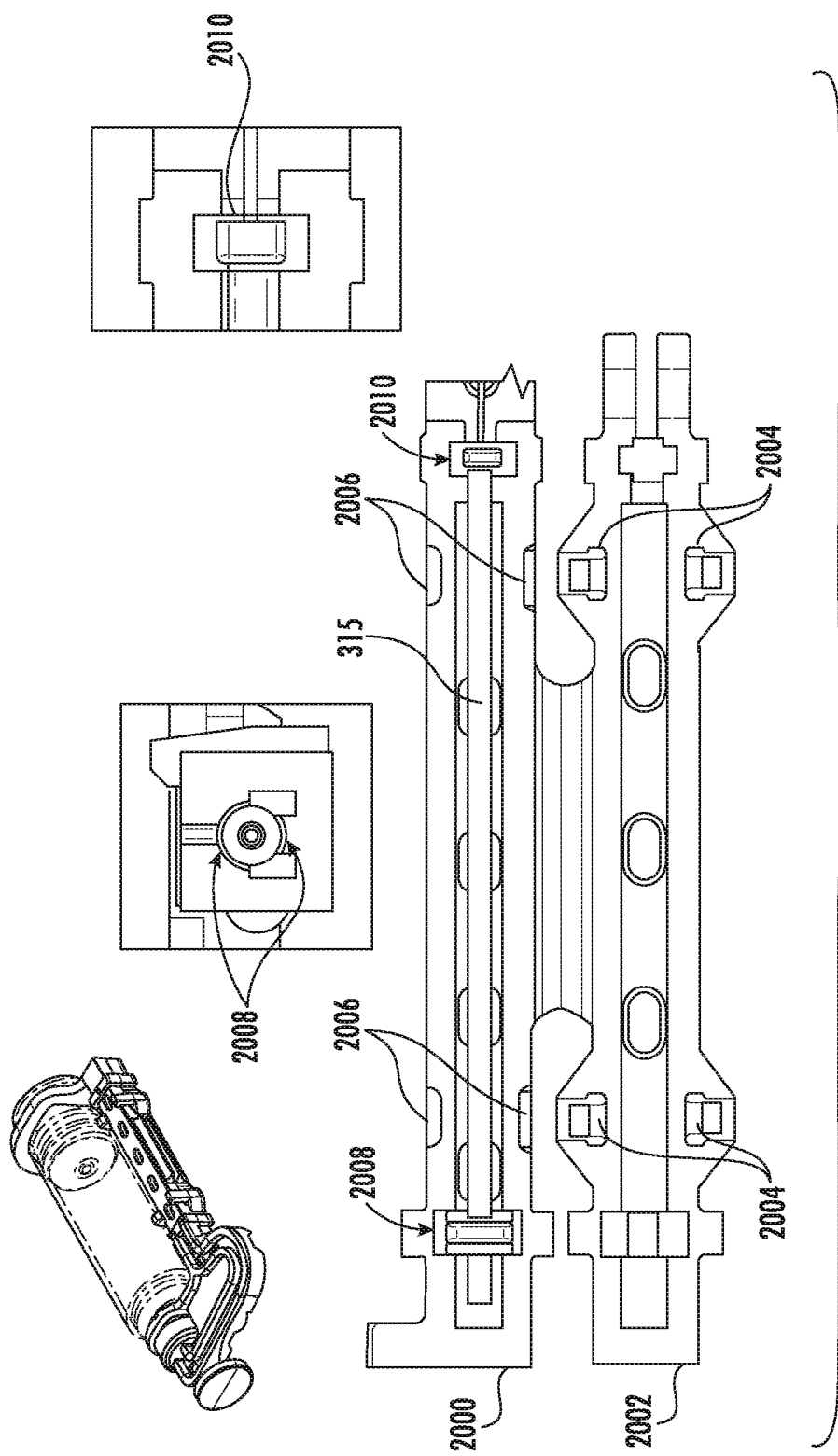
FIG. 20 illustrates an aspect of an exemplary carrier device for use in sterilizing the cartridge and needle cannula portion of a drug delivery device, in accordance with an embodiment of the present disclosure.

FIG. 20 illustrates the manner in which the sterile barrier 315 is coupled to the carrier 1600. Specifically, first and second carrier halves 2000, 2002 can receive respective portions of the sterile barrier 315. The first carrier half 2000 can have a plurality of snap features 2004, while the second carrier half 2002 can have a plurality of snap lead in features 2006. The snap features 2004 and snap lead in features can be sized and positioned so that when the sterile barrier 315 is positioned in the first carrier half 2000, and the second carrier half 2002 is positioned and pressed over the sterile barrier, the snap and snap lead in features engage to hold the first and second carrier halves tightly together. As can be seen, tight radial and axial constraints 2008, 2010 can be held at respective ends of the sterile barrier.

Figure 21:
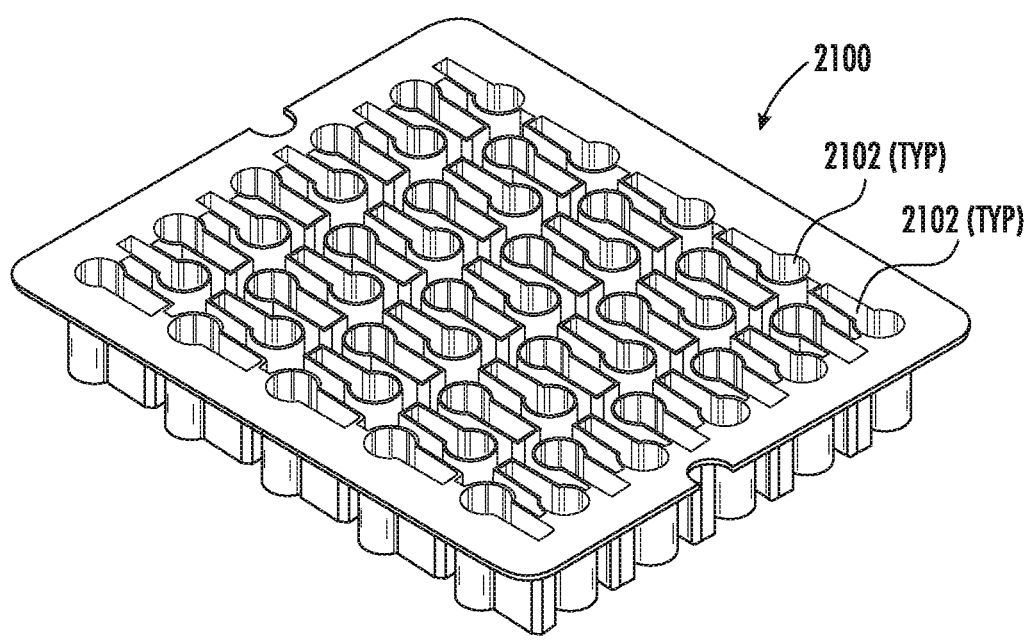
FIG. 21 illustrates an aspect of a nest for use in combination with the carrier element of FIGS. 16-19 to sterilize a cartridge and needle cannula portion of the drug delivery device of FIG. 1, in accordance with an embodiment of the present disclosure.

FIG. 21 shows an exemplary cartridge nest 2100 having a plurality of recesses 2102 for receiving a plurality of carriers 1600 with associated fluid paths. The illustrated nest 2100 can accommodate 50 carriers 1600 with associated fluid paths. The recesses 2102 may be configured to ensure known and repeatable placement of the carriers and fluid paths.

Figure 22:
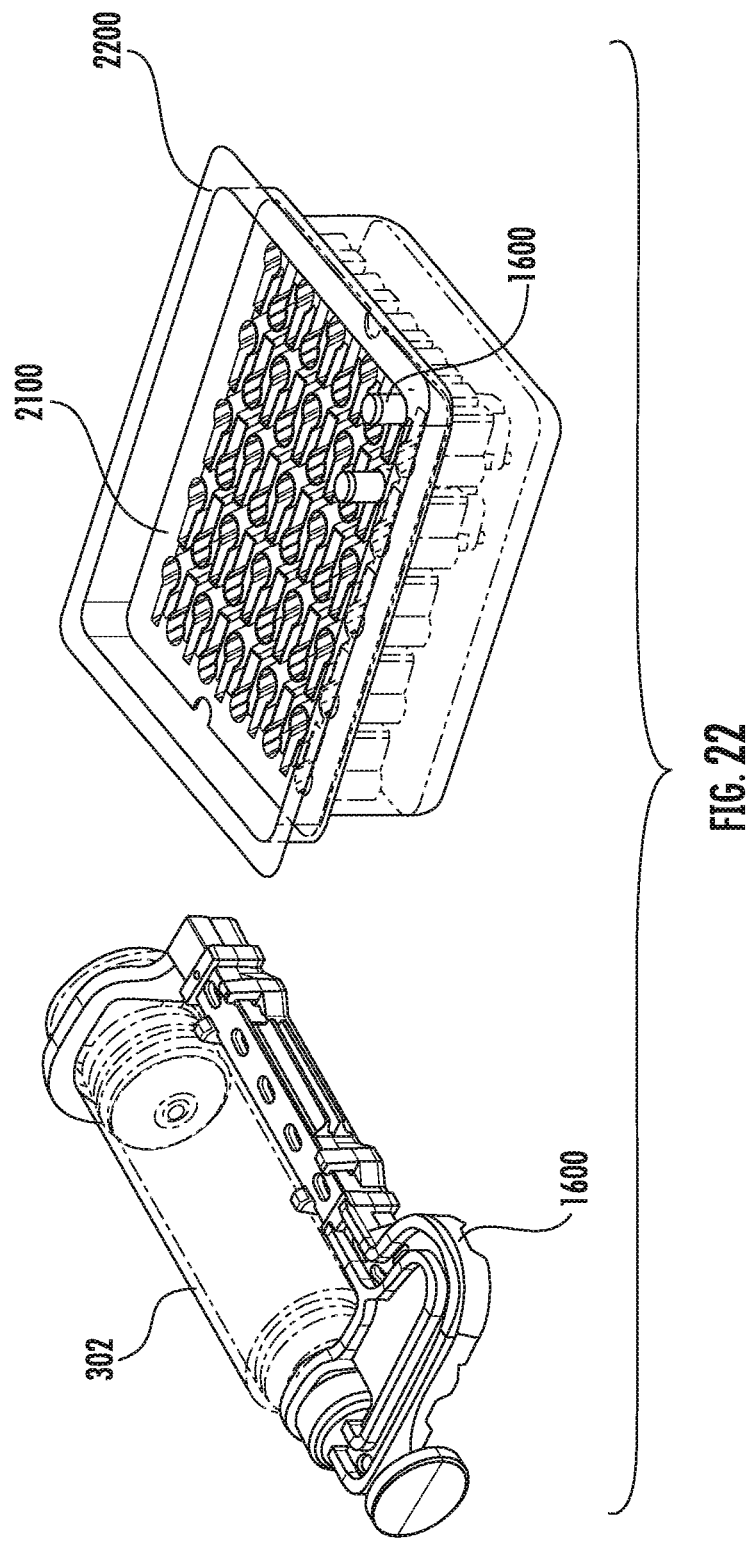
FIG. 22 illustrates an aspect of a nest and carrier, in accordance with an embodiment of the present disclosure.

FIG. 22 shows the exemplary cartridge nest 2100 engages with four individual carriers 1600 and their associated fluid paths. The nest is disposed in a tub 2200, which may be sealable with a permeable membrane (such as Tyvek), permeable by steam, to house all carriers 1600 and their associated fluid paths in handling and sterilization.

In some embodiments, the cartridge nest 2100, tub 2200, carriers 1600 and associated fluid paths may be subjected to moist heat, dry heat, or other appropriate sterilization step.

Figure 23:
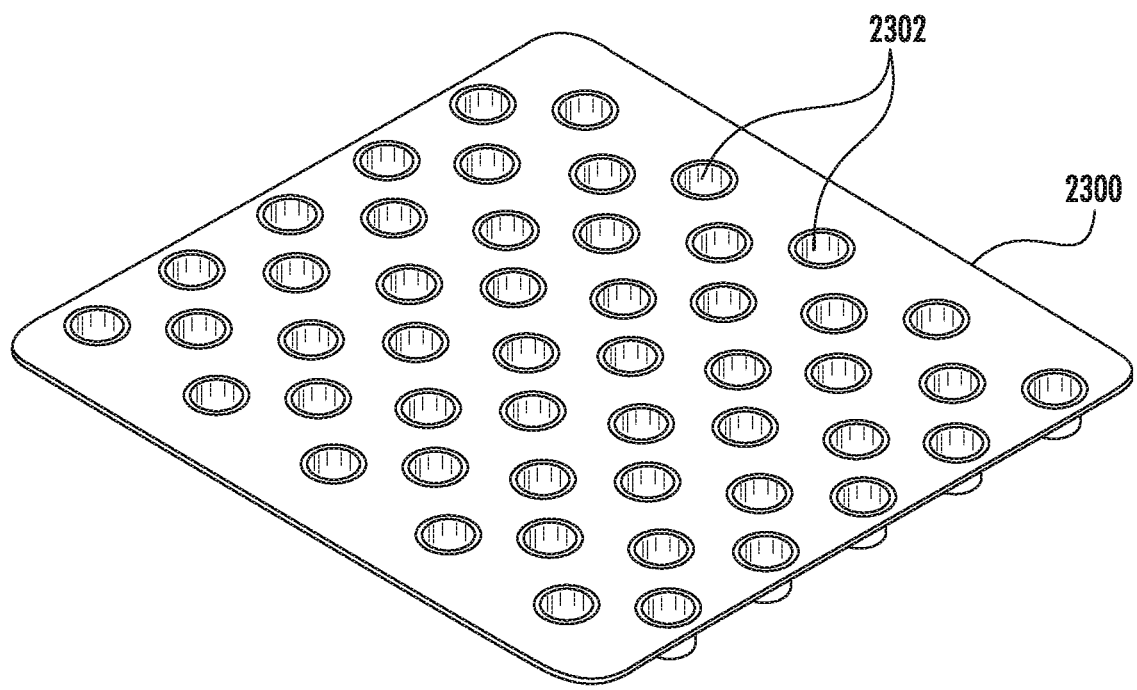
FIG. 23 illustrates an aspect of a nest, in accordance with an embodiment of the present disclosure.

FIG. 23 shows an exemplary plunger nest 2300, which can have a plurality of recesses 2302 to align plungers 308 (FIG. 3) to exact locations of the liquid drug containers 302 held by the cartridge nest 2100. Plungers can then be pressed into engagement with the liquid drug container.

Figure 24:
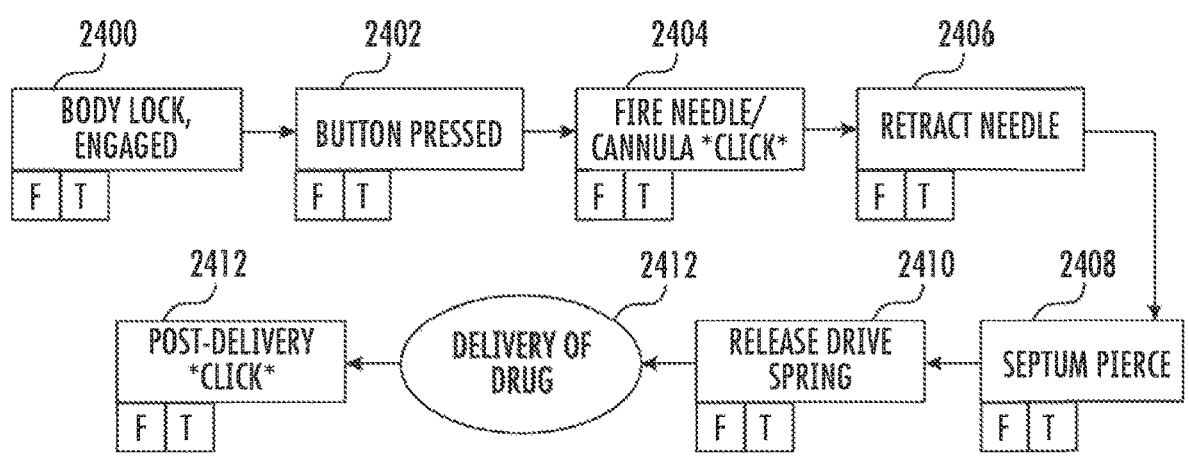
FIG. 24 illustrates an exemplary flow chart of the manner of operating a drug delivery, in accordance with an embodiment of the present disclosure.

FIG. 24 illustrates an exemplary flow chart of the manner of operating the drug delivery device 100 of the present disclosure. At step 2400, the on-body interlock device 110 is engaged such as by pressing and/or adhering the drug delivery device 100 to a patient. At step 2402, the user engagement feature 108 is pressed by the user. At step 2404 the needle insertion mechanism 1006 is activated to insert the needle and a soft cannula. At step 2406, the needle retraction mechanism 1008 retracts the needle, leaving the soft cannula in place. At step 2408, the septum piercing mechanism 312 moves the needle conduit 314 to pierce the septum 311 of the liquid drug container 302, exposing the liquid drug 310 to the needle conduit 314. At step 2410, the drive spring release mechanism 800 is activated to release the drive spring 302. At step 2412, the force transmitting elements 320 press the plunger 308 into the liquid drug container to expel the liquid drug 310 out through the needle conduit 314. At step 2414, when the liquid drug 310 is fully expelled, a tactile and/or audible feedback is provided to the user.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A drive spring release mechanism for use with a drug delivery device, the drive spring release mechanism comprising:
   a drive spring;
   a drive mechanism lock;
   a spring retainer; and
   a drive mechanism release including a cam surface within the drive spring,
   wherein the spring retainer has first and second longitudinally extending spring arms that are biased inward, and which extend to engage the cam surface of the drive mechanism release;
   wherein when the drive spring release mechanism is in a locked state, the cam surface forces distal ends of the spring arms outward so that portions of the distal ends engage associated stop surfaces of the drive mechanism lock, thereby capturing the drive spring therebetween to maintain the drive spring in a compressed state.

2. The drive spring release mechanism of claim 1, wherein when the drive spring release mechanism is in an unlocked state, the drive mechanism release is rotated from its position in the locked state, so that the cam surface releases the distal ends of the spring arms such that the first and second longitudinally extending spring arms flex inward toward each other such that the distal ends of the first and second longitudinally extending spring arms clear the associated stop surfaces of the drive mechanism lock, thereby releasing the drive spring so that it can expand.

3. The drive spring release mechanism of claim 2, wherein when released the drive spring is operable to expand enabling the drive spring to push the spring retainer, which pushes force transmitting elements into a liquid drug container to dispense a liquid drug contained in the liquid drug container.

4. The drive spring release mechanism of claim 2, further comprising a cam extension extending longitudinally from the drive mechanism release, the cam extension having a width less than a distance between the spring arms in the unlocked state.

5. The drive spring release mechanism of claim 4, wherein the cam extension is operable to spread apart the first and second longitudinally extending spring arms enabling insertion of the cam surface.

6. The drive spring release mechanism of claim 1, wherein the portions of the distal ends of each spring arm include a jog shaped to transition from a substantially longitudinal direction, to a substantially radial direction, and to a another substantially longitudinal direction.

7. The drive spring release mechanism of claim 6, wherein a portion of the jog is in a substantially radial direction and engages respective associated stop surfaces of the drive mechanism lock when in the locked state.

8. The drive spring release mechanism of claim 1, further comprising an arm extension extending radially from an end of the drive mechanism lock configured for radial translation.

9. The drive spring release mechanism of claim 1, wherein the portions of the distal ends of each of the first and second longitudinally extending spring arms include two sections that are offset radially and a jog that transitions between the two sections.

10. The drive spring release mechanism of claim 1, wherein, when the drive spring release mechanism is in an unlocked state, the drive spring is operable to expand and push the spring retainer down a track to engage force transmitting elements.

11. A drug delivery device, comprising:
a drug container for storing a liquid drug, wherein a first end of the drug container is sealed by a plunger;
a needle conduit coupled to the drug container;
a needle insertion component coupled to the needle conduit; and
a drive mechanism coupled to the plunger and including a drive spring release mechanism, wherein the drive spring release mechanism includes:
a drive spring;
a drive mechanism lock;
a spring retainer; and
a drive mechanism release including a cam surface within the drive spring,
wherein:
the spring retainer has first and second longitudinally extending spring arms which extend to engage the cam surface of the drive mechanism release, and when the drive spring release mechanism is in a locked state, the cam surface forces distal ends of the spring arms outward so that portions of the distal ends engage associated stop surfaces of the drive mechanism lock, thereby capturing the drive spring therebetween to maintain the drive spring in a compressed state.

12. The drug delivery device of claim 11, wherein when the drive spring release mechanism is in an unlocked state, the drive mechanism release is rotated from its position in the locked state, so that the cam surface releases the distal ends of the spring arms such that the first and second longitudinally extending spring arms flex inward toward each other such that the distal ends of the first and second longitudinally extending spring arms clear the associated stop surfaces of the drive mechanism lock, thereby releasing the drive spring so that it can expand.

13. The drug delivery device of claim 12, wherein releasing the drive spring so that it can expand allows the drive spring to push the spring retainer, which pushes force transmitting elements into the drug container to dispense the liquid drug contained in the drug container.

14. The drug delivery device of claim 12, further comprising a cam extension extending longitudinally from the drive mechanism release, the cam extension having a width less than a distance between the first and second longitudinally extending spring arms in the unlocked state.

15. The drug delivery device of claim 14, wherein the cam extension is operable to spread apart the first and second longitudinally extending spring arms enabling insertion of the cam surface.

16. The drug delivery device of claim 11, wherein the portions of the distal ends of each spring arm include a jog shaped to transition from a substantially longitudinal direction, to a substantially radial direction, and to another substantially longitudinal direction.

17. The drug delivery device of claim 16, wherein a portion of the jog in the substantially radial direction engages the associated stop surfaces of the drive mechanism lock when in the locked state.

18. The drug delivery device of claim 11, further comprising an arm extension extending radially from an end of the drive mechanism lock configured for radial translation.

19. The drug delivery device of claim 11, wherein the portions of the distal ends of each of the first and second longitudinally extending spring arms include two sections that are offset radially, and a jog that transitions between the two sections.

20. The drug delivery device of claim 11, wherein the spring arms are biased inward.

* * * * *